United States Patent
Jalan et al.

(10) Patent No.: US 11,714,087 B2
(45) Date of Patent: Aug. 1, 2023

(54) TREATMENT OF NECROPTOSIS

(71) Applicants: Rajiv Jalan, London (GB); Fausto Andreola, London (GB); Stewart MacDonald, London (GB); Takayuki Kondo, London (GB)

(72) Inventors: Rajiv Jalan, London (GB); Fausto Andreola, London (GB); Stewart MacDonald, London (GB); Takayuki Kondo, London (GB)

( * ) Notice: Subject to any disclaimer, the term of this patent is extended or adjusted under 35 U.S.C. 154(b) by 41 days.

(21) Appl. No.: 17/026,592

(22) Filed: Sep. 21, 2020

(65) Prior Publication Data
US 2021/0072242 A1 Mar. 11, 2021

Related U.S. Application Data

(63) Continuation of application No. PCT/GB2019/050815, filed on Mar. 21, 2019.

(30) Foreign Application Priority Data

Mar. 21, 2018 (GB) ..................................... 1804515

(51) Int. Cl.
G01N 33/573 (2006.01)
A61P 1/16 (2006.01)
A61K 31/4178 (2006.01)
A61K 45/06 (2006.01)

(52) U.S. Cl.
CPC ....... *G01N 33/573* (2013.01); *A61K 31/4178* (2013.01); *A61K 45/06* (2013.01); *A61P 1/16* (2018.01); *G01N 2333/912* (2013.01); *G01N 2800/085* (2013.01); *G01N 2800/50* (2013.01); *G01N 2800/52* (2013.01)

(58) Field of Classification Search
CPC ........ A61K 31/4178; A61K 45/06; A61P 1/16
See application file for complete search history.

(56) References Cited

U.S. PATENT DOCUMENTS

| | | |
|---|---|---|
| 5,503,978 A | 4/1996 | Schneider et al. |
| 5,567,588 A | 10/1996 | Gold et al. |
| 5,654,151 A | 8/1997 | Allen et al. |
| 10,787,462 B2 * | 9/2020 | Yogo .......................... A61P 1/16 |

FOREIGN PATENT DOCUMENTS

| | | |
|---|---|---|
| CN | 103520162 B | 11/2015 |
| WO | 96/38579 A1 | 12/1996 |
| WO | 2009/067245 A2 | 5/2009 |
| WO | WO-2010111599 A2 * | 9/2010 ........... A61K 31/404 |

OTHER PUBLICATIONS

Takemoto et al., "Necrostatin-1 protects against reactive oxygen species (ROS)-induced hepatotoxicity in acetaminophen-induced acute liver failure", FEBS Open Bio, vol. 4, pp. 777-787 (2014).*

Deutsch et al., Divergent effects of RIP1 or RIP3 blockade in murine models of acute liver injury. Cell Death Dis. 2015; 6:e1759, 11 pages.

Fayaz et al., Novel RIPK3 inhibitors discovered through a structure-based approach exert post-ischemic neuroprotection. Mol. Divers. 2016; 20(3):719-728.

Harris et al., Discovery of Small Molecule RIP1 Kinase Inhibitors for the Treatment of Pathologies Associated with Necroptosis. ACS Med. Chem. Lett. 2013; 4(12):1238-1243.

Hu et al., Identification of pyroptosis inhibitors that target a reactive cysteine in gasdermin D. bioRxiv Jul. 10, 2018; https://doi.org/10.1101/365908 [Preprint], 37 pages.

International Search Report issued in connection with corresponding International Application No. PCT/GB2019/050815, dated Aug. 12, 2019, 2 pages.

Khanam et al., 65th Annual Meeting of the American Association for the Study of Liver Diseases, vol. 60, 2014, AASLD, p. 552A, 725, "TNF-alpha induces Receptor Interacting Protein-3 Kinase to mediate necrotic cell death in acute-on-chronic liver failure".

Kopalli et al., Necroptosis inhibitors as therapeutic targets in inflammation mediated disorders—a review of the current literature and patents. Expert Opinion on Therapeutic Patents 2016; 26(11):1239-1256.

Maddox et al., Elevated serum levels in human pregnancy of a molecule immunochemically similar to eosinophil granule major basic protein. J. Exp. Med. 1983; 158(4):1211-1226.

Park et al., HS-1371, a novel kinase inhibitor of RIP3-mediated necroptosis. Exp. Mol. Med. 2018; 50(9):125, 15 pages.

Saeed et al., Necroptosis: an emerging type of cell death in liver diseases. World J. Gastroenterol. 2014; 20(35):12526-12532.

Yang et al., Mechanism of gasdermin D recognition by inflammatory caspases and their inhibition by a gasdermin D-derived peptide inhibitor. PNAS 2018; 115:6792-6797.

(Continued)

*Primary Examiner* — Kevin E Weddington
(74) *Attorney, Agent, or Firm* — Kilpatrick Townsend & Stockton LLP

(57) ABSTRACT

The present invention derives from the unexpected finding that necroptosis is a novel biomarker and target for therapy in patients with liver failure such as acute liver failure (ALF) and acute-on-chronic liver failure (ACLF). RIPK1, MLKL or RIPK3 can be detected and quantified in serum or plasma, and used as a biomarker for outcome in ACLF and other diseases involving aberrant necroptosis. By antagonising RIPK1, MLKL or RIPK3 many of the unwanted consequences or symptoms of acute-on-chronic liver failure (ACLF) may be reduced. The present invention utilises these findings to identify and provide antagonists of RIPK1, MLKL and RIPK3 that may be used in the treatment or prevention of ACLF. The present invention utilises these findings to identify and provide antagonists of RIPK1, MLKL or RIPK3 that may be used in the treatment or prevention of aberrant necroptosis in the kidney, brain, liver or other organ of the body.

5 Claims, 15 Drawing Sheets

(56) References Cited

OTHER PUBLICATIONS

Zheng et al., 66th Annual Meeting of the American Association for the Study of Liver Diseases, vol. 62, 2015, AASLD, p. 1072A, 1772, "The Receptor Interacting Protein Kinase 3 is a critical early warning signs for onset process of acute-on-chronic hepatitis B liver failure".

Zheng et al., 68th Annual Meeting of the American Association for the Study of Liver Diseases, vol. 66, 2017, AASLD, p. 782A-783A, 1465 "Pathophysiological role of Receptor Interacting protein kinase 3 derived necroptosis in the acute on chronic liver failure related with Hepatitis B virus independently of NKT/NK cells".

Arroyo et al., Acute-on-Chronic Liver Failure. N Engl J Med 2020;382:2137-45.

Gustot et al., Transition to decompensation and acute-on-chronic liver failure: Role of predisposing factors and precipitating events. Journal of Hepatology 2021, vol. 75, S36-S48.

Moreau et al., Acute-on-Chronic Liver Failure Is a Distinct Syndrome That Develops in Patients with Acute Decompensation of Cirrhosis. Gastroenterology 2013, vol. 144, No. 7, 1426-1437.

\* cited by examiner

Fig. 1A
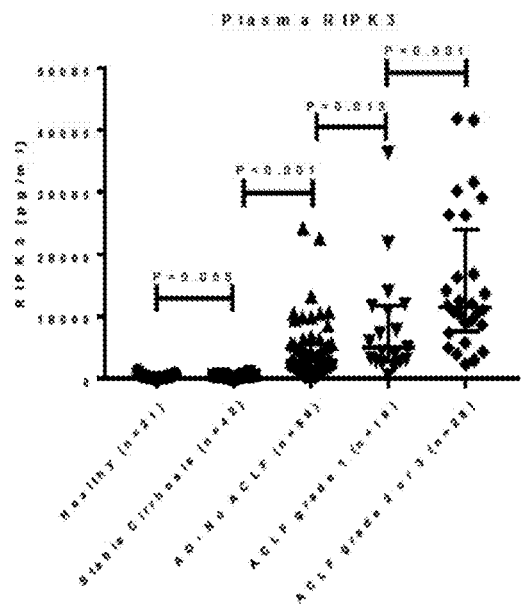
Fig. 1B
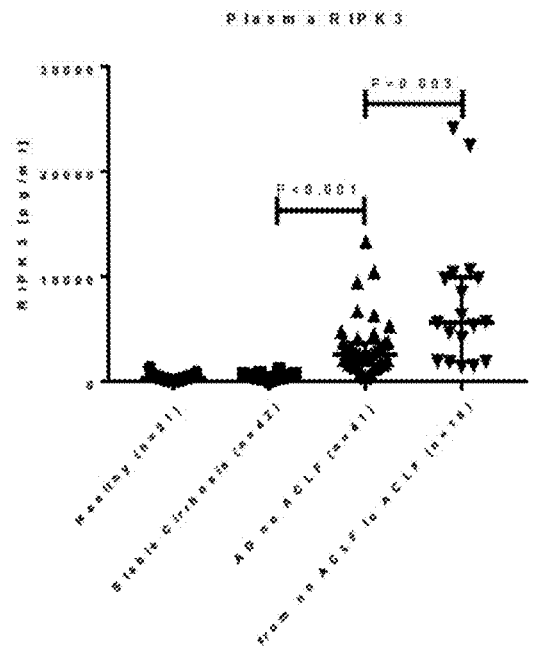
Fig. 1C
|  | RIPK3 (pg/ml) Median (IQR) |
|---|---|
| Healthy controls (n=21) | 322 (136-493) |
| Stable cirrhosis (n=42) | 445 (320-565) |
| All decompensated (n=106) | 4559 (2302-10604) |
| P value | <0.001 |
| | |
| No ACLF (n=59) | 2804 (1665-5551) |
| ACLF grade 1 (n=19) | 5055 (2807-11733) |
| ACLF grade 2 or 3 (n=28) | 11438 (7639-23940) |
| P value | <0.001 |
| | |
| AD throughout (n=41) | 2513 (1563-3680) |
| AD to ACLF (n=18) | 5597 (1894-9972) |
| P value | 0.003 |

TREATMENT OF NECROPTOSIS

FIELD OF THE INVENTION

The present invention derives from the unexpected finding that necroptosis is a novel biomarker and target for therapy in liver failure such as acute liver failure (ALF) and acute-on-chronic liver failure (ACLF). RIPK1, MLKL or RIPK3 can be detected and quantified in serum or plasma, and used as a biomarker for outcome in ACLF and other diseases involving aberrant necroptosis.

By antagonising RIPK1, MLKL or RIPK3 many of the unwanted consequences or symptoms of liver failure such as acute liver failure (ALF) and acute-on-chronic liver failure (ACLF) may be reduced.

The present invention utilises these findings to identify and provide antagonists of RIPK1, MLKL and RIPK3 that may be used in the treatment or prevention of liver failure such as acute liver failure (ALF) and ACLF.

The present invention utilises these findings to identify and provide antagonists of RIPK1, MLKL or RIPK3 that may be used in the treatment or prevention of aberrant necroptosis in the kidney, brain, liver or other organ of the body.

BACKGROUND TO THE INVENTION

An acute decompensating event ((AD), bacterial infection, large-volume ascites, GI haemorrhage, or hepatic encephalopathy, alone or in combination) is the most common hospital presentation of cirrhotic liver disease and can be successfully managed in most cases. However, 30% of patients present with or develop rapidly progressive hepatic and/or extra-hepatic organ failure, a condition referred to as acute-on-chronic liver failure (ACLF). About 20% of these patients progress to multi-organ failure and death. There are currently no specific treatments for ACLF.

Acute-on-chronic liver failure (ACLF) affects about 1 in 3 patients hospitalised with a complication of cirrhosis, and has a 28-day mortality>30%. The pathobiology of ACLF is characterised by translocation of gut-derived bacteria and bacterial products (such as lipopolysaccharide-LPS) to the liver via portal blood, promoting pro-inflammatory responses through the TLR4-dependent canonical inflammasome on immune cells, as well as the TLR4-independent non-canonical inflammasome in hepatocytes.

ACLF is diagnosed by use of the Chronic Liver Failure (CLiF) Consortium criteria, NACSELD criteria or APASL criteria. Previously validated scores to assess disease severity include Child-Pugh (CP) classification, Model for End Stage Liver Disease (MELD) and the CLiF Consortium Acute Decompensation (CLIF-C AD) score.

Necroptosis is a form of non-apoptotic programmed cell death that results in a release of potentially pro-inflammatory cell contents that could trigger inflammation, accelerating further cell death, and organ failure. RIPK1 and RIPK3 are known to be central to the necroptotic pathway as RIPK1 forms an intracellular complex with RIPK3 to assemble the necrosome, an amyloid-like structure that acts as the transducer of the necroptotic signal. Downstream of RIPK3 is another protein, mixed-lineage kinase domain-like protein (MLKL), a pseudokinase that, once phosphorylated, causes necroptosis.

Necroptosis can be induced by several death ligand stimuli (such as TNF, FasL, TRAIL), pathogen-associated molecular patterns such as LPS via TLRs activation or virus-mediated activation under particular conditions (Caspase-8 inhibition, FADD/caspase-8/FLIPL deletion, or RIPK3/MLKL upregulation). Binding of ligands to death receptors (such as TRAIL-R, TNF-R and TLRs) leads to the intracellular formation of complex I. In the next step, under conditions where caspase-8 activity is inhibited or RIPK3 is highly expressed, RIPK1 interacts with RIPK3 to form complex II (necrosome), which mediates necroptosis. This necrosome complex II, consisting of FADD, inactive caspase-8, RIPK1 and RIPK3, allowing RIPK1/3 phosphorylation and the formation of microfilamentous structures leading to RIPK3 oligomerization. MLKL is then recruited on active RIPK3, which phosphorylates MLKL allowing its translocation to the plasma membrane and oligomerization leading to plasma membrane and cell rupture. In parallel, RIPK1, RIPK3 and MLKL promote ROS production, which further enhance necrosome stabilization in a positive feedback loop.

SUMMARY OF THE INVENTION

The present invention is based on the finding that necroptosis is an important mode of cell death in patients with liver failure such as acute liver failure (ALF) and acute-on-chronic liver failure (ACLF). This invention relates to markers of necroptosis as a biomarker and necroptosis itself as a target for therapy in patients with liver failure such as ALF and ACLF. Necroptosis is a recently described non-apoptotic mode of cell death. Hepatocyte necroptosis has a role in the progression of ACLF. They have found that necroptotic cell death is a key mechanism in ACLF, and RIPK1, MLKL and RIPK3 are therapeutic targets in liver failure such as ALF and ACLF.

Accordingly, the invention provides an antagonist of the necroptotic signalling cascade for use in a method of treating or preventing liver failure such as ALF and ACLF or for treating an individual suffering from liver failure such as ALF and ACLF.

In particular, the invention provides an antagonist of RIPK1, MLKL or RIPK3 for use in a method of treating or preventing liver failure such as ALF and ACLF or for treating an individual suffering from liver failure such as ALF and ACLF.

Similarly, the invention provides the use of an antagonist of RIPK1, MLKL or RIPK3 in the manufacture of a medicament for use in the treatment or prevention of liver failure such as ALF and ACLF or the treatment of an individual suffering from liver failure such as ALF and ACLF.

Similarly, the invention provides a method of treating or preventing liver failure such as ALF and ACLF in an individual in need thereof, said method comprising a step of administering to said individual an antagonist of RIPK1, MLKL or RIPK3.

Also the invention provides the use of an antagonist of RIPK1, MLKL or RIPK3 in the manufacture of a medicament for use in the treatment or prevention of liver failure such as ALF and ACLF or the treatment of an individual suffering from liver failure such as ALF and ACLF.

Similarly, the invention provides a method of treating or preventing liver failure such as ALF and ACLF in an individual in need thereof, said method comprising a step of administering to said individual an antagonist of RIPK1, MLKL or RIPK3.

In one particular embodiment, the invention provides an antagonist of RIPK1, MLKL or RIPK3 as described herein for use in the treatment or prevention of liver failure such as ALF and ACLF.

In addition, the invention provides antagonists of RIPK1, MLKL or RIPK3 that may be used in the treatment or prevention of aberrant necroptosis in the kidney, brain, liver or other organ of the body of an individual suffering from a disease or condition characterised by aberrant necroptosis.

Similarly, the invention provides the use of an antagonist of RIPK1, MLKL or RIPK3 in the manufacture of a medicament for use in the treatment or prevention of aberrant necroptosis or the treatment of an individual suffering from aberrant necroptosis.

Similarly, the invention provides a method of treating or preventing aberrant necroptosis in an individual in need thereof, said method comprising a step of administering to said individual an antagonist of RIPK1, MLKL or RIPK3.

The antagonist for use in accordance with the invention may lead to: (a) decreased expression of RIPK1, MLKL or RIPK3 in the immune cells and/or peripheral blood liver and/or kidney and/or brain of the individual; and/or (b) decreased levels of RIPK1, MLKL or RIPK3 in the immune cells and/or peripheral blood and/or liver and/or kidney and/or brain of the individual; and/or (c) decreased activity of RIPK1, MLKL or RIPK3 in the immune cells and/or peripheral blood and/or liver and/or kidney and/or brain of the individual. This would result in reduced inflammation and generation of pro-inflammatory cytokines and reduced dysfunction of organs such as the immune cells and/or peripheral blood and/or liver and/or kidneys and/or brain.

The invention also provides a method of diagnosing liver failure such as ALF and ACLF or predicting the occurrence of liver failure such as ALF and ACLF in a patient and the prognosis of liver failure such as ALF and ACLF in the patient, the method comprising: (a) measuring the level of RIPK3 in the serum or plasma of the patient, and (b) comparing the level of (a) with a known level of RIPK3 from the serum or plasma of a control patient not suffering from ACLF, wherein an increased level in (a) compared to the control indicates that the patient has liver failure such as ALF and ACLF or that the patient is at increased risk of liver failure such as ALF and ACLF, or defines the severity on liver failure such as ALF and ACLF.

The invention also provides a method of identifying a patient suitable for treatment according to the present invention, the method comprising: (a) measuring the level of RIPK3 in the serum or plasma of the patient, and (b) comparing the level of (a) with a known level of RIPK3 from the serum or plasma of a control patient not suffering from liver failure such as ALF and ACLF, wherein an increased level in (a) compared to the control indicates that the patient may be suitable for treatment according to the present invention. Thus, the patient to be treated in accordance with the present invention may be a patient having an increased level of serum or plasma RIPK3 compared to the level of RIPK3 in the serum or plasma of a control patient, such as a healthy patient, such as a patient not suffering from liver failure such as ALF and ACLF.

The invention also provides a method of identifying an agent suitable for use in treating or preventing liver failure such as ALF and ACLF, the method comprising determining whether a test agent is capable of decreasing the amount or activity of RIPK1, MLKL or RIPK3, wherein the ability to decrease the amount or activity of RIPK1, MLKL or RIPK3 indicates that the compound may be suitable for use in treating liver failure such as ALF and ACLF. In such a method, the amount or activity of RIPK1, MLKL or RIPK3 may be assessed in the liver or other organ of the body. A screening method of the invention may comprise administering the test agent to a bile duct ligated rat and determining whether the presence of the test agent leads to a decrease in the amount or activity of RIPK1, MLKL or RIPK3 in the liver of the rat.

BRIEF DESCRIPTION OF THE DRAWINGS

FIGS. 1A-1C—RIPK3 plasma levels stratified by patient group. (FIG. 1A) RIPK3 plasma levels in healthy volunteers, stable cirrhotic patients, patients with acute decompression (AD) but not ACLF and ACLF patients with increasing clinical severity. (FIG. 1B) RIPK3 plasma levels in healthy volunteers, stable cirrhotic patients, patients with acute decompression but not ACLF and patients with AD that subsequently developed ACLF during hospitalisation. (FIG. 1C) Summary of results.

(FIG. 3A) Plasma levels of RIPK3 in a rodent model of ACLF. (FIG. 3B) RIPK1 and RIPK3 staining in a rodent model of ACLF (10× and 40× magnification).

(FIG. 4A) Representative images of liver tissue of sham, BDL, BDL+LPS and BDL+NEC-1+LPS stained for RIPK1 (magnification, 10× and 40×). The optical density of RIPK1 and RIPK3 immunostaining intensity (mean±SEM). (FIG. 4B) Representative images of liver tissue of sham, BDL, BDL+LPS and BDL+NEC-1+LPS of TUNEL staining (magnification, 10× and 40×). The optical density of TUNEL staining intensity (mean±SEM). (FIGS. 4C-4D) Plasma levels of RIPK3, nucleosomes and histone 3 of sham, BDL, BDL+LPS and BDL+NEC-1+LPS (mean±SEM). (FIG. 4E) Plasma levels of AST and albumin of sham, BDL, BDL+LPS and BDL+NEC-1+LPS (mean±SEM). Data were analyzed using Student's t test or Mann-Whitney U test. *$p<0.05$, $p<0.01$, *$p<0.001$.

(FIG. 5A) Representative images of kidney tissue of sham, BDL, BDL+LPS and BDL+NEC-1+LPS of TUNEL staining (magnification, 10× and 40×). The optical density of TUNEL staining intensity (mean±SEM). (FIG. 5B) Plasma levels of creatinine and urea of sham, BDL, BDL+LPS and BDL+NEC-1+LPS (mean±SEM). (FIG. 5C) Brain water of BDL+LPS and BDL+NEC-1+LPS (mean±SEM). Data were analyzed using Student's t test or Mann-Whitney U test. *$p<0.05$, $p<0.01$, *$p<0.001$.

(FIG. 7A) Plasma levels of RIPK3 of rat models of sham, BDL and BDL+LPS (mean±SEM). (FIG. 7B) Nucleosome levels of rat models of sham, BDL and BDL+LPS (mean±SEM). (FIG. 7C) Representative images of kidney tissues of rat models of sham, BDL and BDL+LPS stained for RIPK1 and RIPK3 (magnification, 10× and 40×). (FIG. 7D) The optical density of RIPK1 and RIPK3 immunostaining intensity (mean±SEM) in liver. Data were analyzed using Student's t test or Mann-Whitney U test. *p<0.05, p<0.01, *p<0.001. (FIG. 7E) The optical density of RIPK1 and RIPK3 immunostaining intensity (mean±SEM) in kidney. Data were analyzed using Student's t test or Mann-Whitney U test. *p<0.05, p<0.01, *p<0.001.

(FIG. 9A) Predisposition factor (FIG. 9B) Injury-precipitating factor (FIG. 9C) Response (FIG. 9D) Type of organ failure (single organ failure) Data were analyzed using Student's t test, Mann-Whitney U test or Kruskal-Wallis test followed by Fisher's Least Significant Difference test. *p<0.05, p<0.01, *p<0.001.

DETAILED DESCRIPTION OF THE INVENTION

Figure 2:
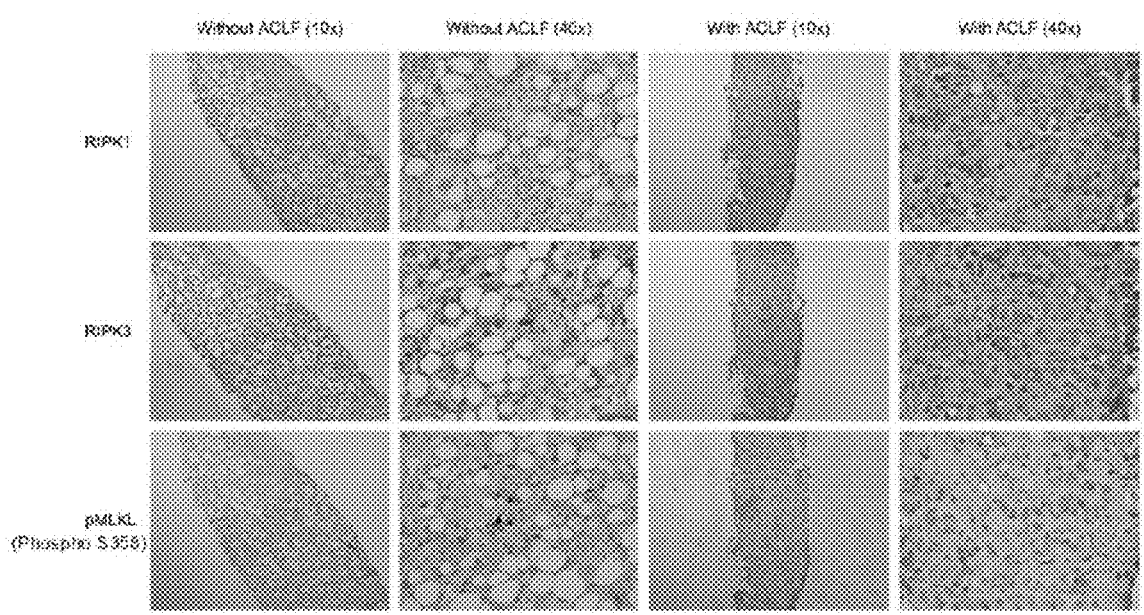
FIG. 2—RIPK1, RIPK3 and pMLKL (phosphorylated MLKL) staining of liver biopsies in patients with alcoholic hepatitis with and without ACLF (10× and 40× magnification). Increased expression of both RIPK1 and RIPK3 was observed in the liver biopsies of patients with ACLF in addition to alcoholic hepatitis, compared to the biopsies of patients with alcoholic hepatitis and no ACLF. The presence of ACLF in addition to alcoholic hepatitis was associated with enhanced expression of phosphorylated MLKL in comparison to alcoholic hepatitis without ACLF.

It is to be understood that different applications of the disclosed methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "an antagonist" includes "antagonists", reference to "an antibody" includes two or more such antibodies, and the like.

All publications, patents and patent applications cited herein, whether supra or infra, are hereby incorporated by reference in their entirety.

The inventors have unexpectedly found that necroptosis is an important mode of cell death in patients with liver failure such as acute liver failure (ALF) and acute-on-chronic liver failure (ACLF). This invention relates to necroptosis as a biomarker and target for therapy in patients with ALF or ACLF. They have found that necroptotic cell death is a key mechanism in liver failure such as ALF and ACLF, and RIPK1, MLKL and RIPK3 are therapeutic targets in liver failure such as ALF and ACLF.

RIPK1

Receptor-interacting serine/threonine-protein kinase 1 (RIPK1) is an enzyme belonging to the Receptor Interacting Protein (RIP) kinases family, which consists of 7 members. RIPK1 is known to have function in a variety of cellular pathways related to both cell survival and death. In terms of cell death, RIPK1 plays a role in apoptosis and necroptosis.

In necroptosis, RIPK1 forms an intracellular complex with RIPK3 to assemble the necrosome, an amyloid-like structure that acts as the transducer of the necroptotic signal.

RIPK3

Receptor-interacting serine/threonine-protein kinase 3 (RIPK3) is an enzyme belonging to the Receptor Interacting Protein (RIP) kinases family, which consists of 7 members.

In necroptosis RIPK3 forms an intracellular complex with RIPK1 to assemble the necrosome, an amyloid-like structure that acts as the transducer of the necroptotic signal.

MLKL

Mixed-lineage kinase domain-like protein (MLKL) belongs to the protein kinase superfamily. Downstream of RIPK3 in the necroptosis pathway is MLKL, a pseudokinase that, once phosphorylated, causes necroptosis. The MLKL protein plays a critical role in necroptosis, via interaction with receptor-interacting protein 3 (RIP3), which is a key signaling molecule in necroptosis pathway. Inhibitor studies and knockdown of the MLKL gene inhibited necrosis.

The present invention relates to the treatment, prevention and or diagnosis of liver failure such as acute-on-chronic liver failure (ACLF) and/or acute liver failure (ALF).

ACLF

Acute-on-chronic liver failure (ACLF) is a distinct clinical entity encompassing an acute deterioration of liver function in patients with cirrhosis, often decompensated cirrhosis, which is usually associated with a precipitating event and results in the failure of one or more organs and high short term mortality. Unregulated inflammation is thought to be a major contributing factor. A characteristic feature of ACLF is its rapid progression, the requirement for multiple organ supports and a high incidence of short and medium term mortality of 50-90%.

Acute Liver Failure (ALF)

Acute Liver Failure (ALF) is widely accepted as a syndrome of rapid decline in liver function characterized by jaundice, coagulopathy (INR>1.5) and hepatic encephalopathy in patients with no evidence of prior liver disease. Acute liver failure is a further condition where it is thought that non-apoptotic forms of cell death play an important role in disease progression and development, and thus present likely therapeutic targets. There are many causes of ALF including drug toxicity, drug overdose, paracetamol overdose, autoimmune hepatitis, viral hepatitis, Wilson's disease, etc.

Aberrant Necroptosis

The present invention provides antagonists of RIPK1, MLKL or RIPK3 that may be used in the treatment or prevention of aberrant necroptosis in the immune system, kidney, brain, liver or other organ of the body. Aberrant necroptosis can be considered to be abnormal or pathogenic necroptosis that occurs as part of a disease or condition. Treating or preventing aberrant necroptosis by administering antagonists of RIPK1, MLKL or RIPK3 to individuals in need thereof thus provides treatment of the underlying disease or condition characterised by aberrant necroptosis. Examples of diseases or conditions characterised by aberrant necroptosis is ALF and ACLF.

The present invention thus derives from the inventors' findings of the role of RIPK1, MLKL and RIPK3 in necroptosis and liver failure such as ALF and ACLF. The present invention utilises these effects by proposing antagonists of RIPK1, MLKL or RIPK3 as therapeutic agents for use in the treatment or prevention of such conditions.

Antagonists of RIPK1, MLKL or RIPK3

The present invention relates to the antagonism of RIPK1, MLKL or RIPK3. An antagonist of RIPK1, MLKL or RIPK3 may be any compound or molecule that inhibits or decreases the activity, function or amount of RIPK1, MLKL or RIPK3. Preferably the antagonist functions in the immune system, liver and/or kidney and/or brain of the patient with liver failure such as ALF and ACLF. The antagonist may act preferentially in the immune system, liver and/or kidney or may act at a number of locations including the immune system, liver and/or kidney and/or brain. Preferably the antagonist leads to a decrease in RIPK1, MLKL or RIPK3 activity, function or amount in the organs of an individual to whom the antagonist is administered, such as in one of more of the immune system, liver, kidneys, brain, and the heart of the individual. The antagonist may be targeted to the liver, kidney or other organs such as those listed above during administration as discussed further below.

Preferred antagonists are those that decrease the activity or amount of RIPK1, MLKL or RIPK3 by at least 10%, at least 20%, at least 30%, at least 40%, at least 50%, at least 60%, at least 70%, at least 80% or at least 90% compared to the amount seen in the absence of the antagonist. For example, decreases of these sizes may be seen in the liver or liver tissue of a subject to whom the agonist has been administered. Decreases of these sizes may be seen in other tissues or organs of the individual, such as in the kidney and/or heart of the individual.

An antagonist of RIPK1, MLKL or RIPK3 may reduce the activity or amount of RIPK1, MLKL or RIPK3 to an amount or activity that is the same, similar to, or equivalent to, that seen in an individual not suffering from liver failure such as ALF and ACLF. For example, as explained herein, the expression of RIPK3 is found to be increased in association with a model of liver failure such as ALF and ACLF. Use of a RIPK3 antagonist in accordance with the present invention may lead to a reduction in RIPK3 expression in the liver and/or kidneys and/or brain of the individual being treated to a normal level, such as a level that would be seen or would be expected in an individual not suffering from liver failure such as ALF and ACLF.

The antagonist may act specifically to antagonise RIPK1, MLKL or RIPK3. That is, the effect of the antagonist on RIPK1, MLKL or RIPK3 may be greater than any other biological effect of the antagonist. Such an antagonist may be specific to the inhibition of RIPK1, MLKL or RIPK3, that is it may decrease the activity of RIPK1, MLKL or RIPK3, but not other related proteins. Such an antagonist may additionally or alternatively be specific to the expression of RIPK1, MLKL or RIPK3, that is it may decrease the expression of RIPK1, MLKL or RIPK3 but not other receptors such as other related proteins. An antagonist for use in accordance with the present invention may be an antagonist of RIPK1, MLKL or RIPK3 as described herein, that does not act as an antagonist of other related proteins. An antagonist for use in accordance with the present invention may act on RIPK1, MLKL or RIPK3 in preference to other related proteins. For example, an antagonist of RIPK1, MLKL or RIPK3 for use in accordance with the present invention may have one or more of the characteristics of an RIPK1, MLKL or RIPK3 antagonist as described herein, but may not have such characteristics in relation to other related proteins, or may have such characteristics to a lower level in relation to other related proteins when compared to RIPK1, MLKL or RIPK3. For example, an antagonist that decreases the activity of RIPK1, MLKL or RIPK3 may not decrease the activity of other related proteins, or may decrease the activity of other related proteins to a lesser extent, such as a lower percentage decrease, than its effect on RIPK1, MLKL or RIPK3. An antagonist that decreases the expression or amount of RIPK1, MLKL or RIPK3 may not decrease the expression or amount of other related proteins, or may decrease the expression of other related proteins a lesser extent, such as a lower percentage decrease, than its effect on RIPK1, MLKL or RIPK3. An RIPK1, MLKL or RIPK3 antagonist as described herein may have an effect on other related proteins, such as antagonism of the activity, signalling or expression of one or more other related proteins, that is less than 25%, less than 20%, less than 15%, less than 10%, less than 5%, less than 1%, or less than 0.1% the effect of that antagonist on the activity, signalling or expression of RIPK1, MLKL or RIPK3.

By other related proteins it is meant other proteins in the same protein families as RIPK1, MLKL or RIPK3. For example, other RIPK family members can be considered as related proteins of RIPK1 or RIPK3.

The specificity of the RIPK1, MLKL or RIPK3 antagonist may apply within the whole body of the individual to be treated, that is the actions of the RIPK1, MLKL or RIPK3 antagonist may be specific as discussed above throughout the body of the individual. The specificity of the RIPK1, MLKL or RIPK3 antagonist may apply within particular tissues of the individual, such as the liver, kidneys and/or heart and/or brain. That is, in one embodiment, the RIPK1, MLKL or RIPK3 antagonist may act specifically to antagonise RIPK1, MLKL or RIPK3 as discussed above within the liver and/or kidney and/or other organs of the individual being treated.

The RIPK1, MLKL or RIPK3 antagonist may therefore be a specific antagonist of RIPK1, MLKL or RIPK3 as described above. For example, the RIPK1, MLKL or RIPK3 antagonist may not be an antagonist of other related proteins, or may have no significant effect on the activity or expression of other related proteins.

Any agent capable of inhibiting the activity or function of RIPK1, MLKL or RIPK3 may be suitable for use in the methods of the present invention. Antagonists for use in accordance with the present invention may be direct or indirect antagonists of RIPK1, MLKL or RIPK3.

Indirect antagonists of RIPK1, MLKL or RIPK3 are agents whose activity is directed to a member of the necroptotic signalling pathway other than RIPK1, MLKL or RIPK3. Inhibition of such members of the necroptotic signalling pathway act to inhibit necroptosis, thus indirectly inhibiting the function of RIPK1, MLKL or RIPK3.

Direct antagonists are agents whose activity is directly on RIPK1, MLKL or RIPK3. For example, direct antagonists may be agents that act directly on RIPK1, MLKL or RIPK3 to decrease its activity. A direct antagonist may be an agent that disrupts RIPK1, MLKL or RIPK3 function or that destabilises interaction of RIPK1, MLKL or RIPK3 with their binding partners. A direct antagonist may decrease the amount of RIPK1, MLKL or RIPK3 by destroying or disrupting RIPK1, MLKL or RIPK3 molecules within the patient. A direct antagonist may be an agent that acts on the RIPK1, MLKL or RIPK3 gene, promoter or other gene regulatory regions to decrease expression of the RIPK1, MLKL or RIPK3. A direct antagonist may decrease expression of RIPK1, MLKL or RIPK3 by preventing or reducing expression from the endogenous RIPK1, MLKL or RIPK3 gene.

A RIPK1, MLKL or RIPK3 antagonist may act to disrupt the activity of RIPK1, MLKL or RIPK3. For example, the antagonist may act by preventing activation of RIPK1, MLKL or RIPK3 or by preventing formation of functional complexes comprising RIPK1, MLKL or RIPK3.

Any agent or molecule having the properties described above may be used as an RIPK1, MLKL or RIPK3 antagonist in accordance with the present invention. The test agent may be, or may comprise, for example, a peptide, polypeptide, protein, antibody, polynucleotide, small molecule or other compound that may be designed through rational drug design starting from known antagonists of RIPK1, MLKL or RIPK3.

Examples of Antagonists of RIPK1, MLKL or RIPK3

The Table below lists some specific examples of necroptosis inhibitors. The Table is taken from Kopalli, Kang and Koppula (2016) Necroptosis inhibitors as therapeutic targets in inflammation mediated disorders—a review of the current literature and patents, Expert Opinion on Therapeutic Patents, 26, pages 1239-1256.

Examples include MAK: *Ganoderma lucidium* Mycelia; IM-54: 1-Methyl-3-(1-methyl-1H-indol-3-yl)-4-(pentylamino)-1H-pyrrole-2,5-dione,2-(1H-Indol-3-yl)-3-pentylamino-maleimide; KA: Kongensin A; NECs: Necrostatins; WETC: Terminalia chebula water extract; NGEN: Naringenin; NSA: Necrosulfonamide, HS-1371 (Park et al. (2018) Experimental and Molecular Medicine 50, 125).

| Compound name | Mode of action |
| --- | --- |
| Necrostatins | |
| Nec-1, Nec-2, Nec-3, Nec-Ts | RIPK1 inhibitor |
| 7-Cl-Nec-1, 7-Cl—O-Nec-1 | RIPK1 inhibitor |
| B-7-Cl—O-Nec-1 | RIPK1 inhibitor |
| Nec-5, Nec-7 | RIPK1 inhibitor |
| Vorinostat | RIPK1 inhibitor |
| Ponatinib and pazopanib | MLKL inhibitor |
| 1-Benzyl-1H-pyrazole derivatives | RIPK1 inhibitor |
| Aminoisoquinolines | RIPK1 inhibitor |
| Furo[2,3-d]pyrimidines | |
| Pyrrolo[2,3-b]pyridines | |
| Necrosulphonamide | MLKL inhibitor |
| IM-54 | Necroptosis-related ROS inhibitor |
| NecroX analogs | |
| NecroX-1, NecroX-2, NecroX-5, NecroX-7 | Necroptosis-related ROS inhibitor |
| PN10 | RIPK1 inhibitor |
| Cpd27 | RIPK1 inhibitor |
| GSK compounds GSK'840, GSK'843, GSK'872 | RIPK1/RIPK3 inhibitor |
| Compound 1 | MLKL inhibitor |
| Natural products and isolated compounds | |
| *Ganoderma lucidium* Mycelia | RIPK3/necroptosis related ROS inhibitor |
| *Terminalia Chebula* | Necroptosis related ROS inhibitor |
| Kongensin A | RIPK3 inhibitor |
| Celastrol | RIPK3/MLKL inhibitor |
| Naringenin | Necroptosis related ROS inhibitor |
| Curcumin | RIPK1/necroptosis-related ROS inhibitor |
| Necroptosis inhibitors-patents | |
| Small molecule necroptosis inhibitors | RPK1 inhibitor |
| Tricyclic necrostatin compounds | |
| Heterocyclic inhibitors of necroptosis | |
| Spiroquinoxaline derivatives | |

ROS: Reactive oxygen species

An antagonist of MLKL may act by inhibiting phosphorylation of MLKL. An antagonist of RIPK1 or RIPK3 may act by inhibiting the interaction between RIPK1 and RIPK3. Small molecule inhibitors of RIPK1 are disclosed in, for example, Harris et al (2013) Discovery of Small Molecule RIP1 Kinase Inhibitors for the Treatment of Pathologies Associated with Necroptosis, ACS Medicinal Chemistry Letters, 4, pages 1238-1243. The Bcr-ABL inhibitor ponatinib is also a dual RIPK1 and RIPK3 inhibitor with cytoprotective properties in RIPK1- and RIPK3-driven cell death, both in vitro and during inflammatory pathology in vivo. Further RIPK3 inhibitors are disclosed in Fayaz et al. (2016) Novel RIPK3 inhibitors discovered through a structure-based approach exert post-ischemic neuroprotection, Molecular Diversity, 20, pages 719-738. An example of an antagonist of MLKL is necrosulfonamide.

The RIPK1, MLKL or RIPK3 antagonist may be a molecule that is capable of binding to and preventing or disrupting the activity of RIPK1, MLKL or RIPK3.

Accordingly, one group of RIPK1, MLKL or RIPK3 antagonists for use in accordance with this invention are anti-RIPK1, MLKL or RIPK3 antibodies. Such an antibody may be monoclonal or polyclonal or may be an antigen-binding fragment thereof. For example, an antigen-binding fragment may be or comprise a F(ab)2, Fab, scFv or Fv fragment, i.e. a fragment of the "variable" region of the antibody, which comprises the antigen binding site. An antibody or fragment thereof may be a single chain antibody, a chimeric antibody, a CDR grafted antibody or a humanised antibody.

An antibody may be directed to the RIPK1, MLKL or RIPK3 molecule, i.e. it may bind to epitopes present on RIPK1, MLKL or RIPK3 and thus bind selectively and/or specifically to RIPK1, MLKL or RIPK3. An antibody may be directed to another molecule that is involved in the expression and/or activity of RIPK1, MLKL or RIPK3. For example, a polyclonal antibody may be produced which has a broad spectrum effect against one or more epitopes on RIPK1, MLKL or RIPK3 and/or one or more other molecules that are involved in the expression and/or activity of RIPK1, MLKL or RIPK3.

Antibodies can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

An antibody, or other compound, "specifically binds" to a molecule when it binds with preferential or high affinity to the molecule for which it is specific but does substantially bind not bind or binds with only low affinity to other molecules. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

The RIPK1, MLKL or RIPK3 antagonist may be an antisense oligonucleotide, such as an antisense oligonucleotide against the gene encoding a RIPK1, MLKL or RIPK3 protein. The term "antisense oligonucleotide" as used herein means a nucleotide sequence that is complementary to the mRNA for a desired gene. Such an antisense oligonucleotide may selectively hybridise with the desired gene. In the context of the present invention, the desired gene may be the gene encoding RIPK1, MLKL or RIPK3.

The RIPK1, MLKL or RIPK3 antagonist may modulate expression of the RIPK1, MLKL or RIPK3 gene. For example, the RIPK1, MLKL or RIPK3 antagonist may be a short interfering nucleic acid (siRNA) molecule, double stranded RNA (dsRNA), micro RNA, deoxyribose nucleic acid interference (DNAi) or short hairpin RNA (shRNA) molecule.

The term "selectively hybridise" as used herein refers to the ability of a nucleic acid to bind detectably and specifically to a second nucleic acid. Oligonucleotides selectively hybridise to target nucleic acid strands under hybridisation and wash conditions that minimise appreciable amounts of detectable binding to non-specific nucleic acids. High stringency conditions can be used to achieve selective hybridisation conditions as known in the art. Typically, hybridisation and washing conditions are performed at high stringency according to conventional hybridisation procedures. Washing conditions are typically 1-3×SSC, 0.1-1% SDS, 50-70° C. with a change of wash solution after about 5-30 minutes.

The RIPK1, MLKL or RIPK3 antagonist may be a nucleic acid molecule such as an antisense molecule or an aptamer. The nucleic acid molecule may bind a specific target molecule.

Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

The terms "nucleic acid molecule" and "polynucleotide" are used interchangeably herein and refer to a polymeric form of nucleotides of any length, either deoxyribonucleotides or ribonucleotides, or analogs thereof. A nucleic acid may comprise conventional bases, sugar residues and internucleotide linkages, but may also comprise modified bases, modified sugar residues or modified linkages. A nucleic acid molecule may be single stranded or double stranded.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by EXonential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579. The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Any of the antagonists described herein may therefore be used to antagonise RIPK1, MLKL or RIPK3, i.e. to decrease the amount of RIPK1, MLKL or RIPK3 that is present, and/or the activity or the function of the RIPK1, MLKL or RIPK3. Preferably these antagonising effects take place in the liver and/or kidney and/or brain.

An antagonist of RIPK1, MLKL or RIPK3 may be an agent that decreases the production of endogenous RIPK1, MLKL or RIPK3. For example, the agent may act within the cells of the subject to inhibit or prevent the expression of RIPK1, MLKL or RIPK3. Such an agent may be a transcription factor or enhancer that acts on the RIPK1, MLKL or RIPK3 gene to inhibit or prevent gene expression.

In some embodiments, the present invention also provides an antagonist of RIPK1, MLKL or RIPK3 in combination with an activator or agonist of caspase-8 for use in a method of treating an individual suffering from acute-on-chronic liver failure (ACLF). In other words, in some embodiments of the present invention, the antagonist of RIPK1, MLKL or RIPK3 may be used or administered in combination with an activator or agonist of caspase-8. Such combinations may be administered sequentially or at the same time. As such, the antagonist of RIPK1, MLKL or RIPK3 may be administered before or after the activator or agonist of caspase-8.

The term "activator of a protein" or "agonist of a protein" within the context of this invention refers to any agent, such as a protein, nucleotide and small molecule, capable of up-regulating said protein production and/or action. For example, an activator of caspase-8 may be a molecule that act upstream of caspase-8. An activator may also be a molecule which binds directly to caspase-8 in order to induce its activation.

Caspase-8 is a member of the broader caspase family, which are a group of cysteine proteases that specifically cleave substrates at sites located after aspartic acid residues in target amino acid sequences. These proteases are well known to play a central role in the apoptotic cell death machinery and caspase-8 has been known to play a role in the extrinsic apoptotic signalling pathway via death receptors.

Examples of activators of caspase-8 include, but are not limited to, FADD, caspases that can cleave caspase-8, that is—caspase-6 and caspase-3 and, indirectly, the various death receptors of the TNF/NGF family. Depending on the exact cellular set up, cFLIP long may also serve as caspase-8 activator.

Screening Methods

The present invention also provides methods for the identification of agents suitable for use in the treatment or prevention of liver failure such as ALF and ACLF. For example, the invention provides methods for the identification of antagonists of RIPK1, MLKL or RIPK3 which are suitable for use in treating liver failure such as ALF and ACLF. Antagonists identified by this method may be antagonists of RIPK1, MLKL or RIPK3 having any of the characteristics or effects described above. Antagonists identified by the methods described herein may be suitable for use in the treatment or prevention of in liver failure such as ALF and ACLF. Antagonists identified by the methods described herein may be suitable for use in the treatment or prevention of aberrant necroptosis.

Accordingly, the invention provides a method of identifying an agent for use in the treatment or prevention of aberrant necroptosis or liver failure such as ALF and ACLF, the method comprising determining whether a test agent is capable of decreasing the activity or expression of RIPK1, MLKL or RIPK3. For example, the method may involve determining whether a test agent is capable of decreasing the amount or activity of RIPK1, MLKL or RIPK3, wherein the ability to decrease the amount or activity of RIPK1, MLKL or RIPK3 indicates that the compound may be suitable for use in treating or preventing aberrant necroptosis or liver failure such as ALF and ACLF as described herein.

A test agent for use in a screening method of the invention refers to any compound, molecule or agent that may potentially antagonise RIPK1, MLKL or RIPK3. The test agent may be, or may comprise, for example, a peptide, polypeptide, protein, antibody, polynucleotide, small molecule or other compound that may be designed through rational drug design starting from known antagonists of RIPK1, MLKL or RIPK3.

The test agent may be any agent having one or more characteristics of an antagonist of RIPK1, MLKL or RIPK3 as described above.

The test agent to be screened could be derived or synthesised from chemical compositions or man-made compounds. Candidate agents may be obtained from a wide variety of sources including libraries of synthetic or natural compounds. Suitable test agents which can be tested in the above assays include compounds derived from combinatorial libraries, small molecule libraries and natural product libraries, such as display (e.g. phage display) libraries. Multiple test agents may be screened using a method of the invention in order to identify one or more agents having a suitable effect on RIPK1, MLKL or RIPK3, such as inhibition of RIPK1, MLKL or RIPK3 activity or expression.

The screening methods of the invention may be carried out in vivo, ex vivo or in vitro. In particular, the step of contacting a test agent with RIPK1, MLKL or RIPK3 or with a cell or tissue that comprises RIPK1, MLKL or RIPK3 may be carried out in vivo, ex vivo or in vitro. The screening methods of the invention may be carried out in a cell-based or a cell-free system. For example, the screening method of the invention may comprise a step of contacting a cell or tissue comprising RIPK1, MLKL or RIPK3 with a test agent and determining whether the presence of the test agent leads to a decrease in the amount or activity of RIPK1, MLKL or RIPK3 in the cell or tissue.

For example, the ability of a test agent to decrease the activity or expression of RIPK1, MLKL or RIPK3 may be tested in a host cell or tissue that expresses RIPK1, MLKL or RIPK3. For example, the amount or activity of RIPK1, MLKL or RIPK3 may be assessed in vitro, in vivo or ex vivo in the liver or in tissue or cells derived from the liver.

In such a cell-based assay, the RIPK1, MLKL or RIPK3 and/or the test agent may be endogenous to the host cell or tissue, may be introduced into a host cell or tissue, may be introduced into the host cell or tissue by causing or allowing the expression of an expression construct or vector or may be introduced into the host cell or tissue by stimulating or activating expression from an endogenous gene in the cell.

In such a cell-based method, the amount of RIPK1, MLKL or RIPK3 may be assessed in the presence or absence of a test agent in order to determine whether the agent is altering the amount of RIPK1, MLKL or RIPK3 in the cell or tissue, such as through regulation of RIPK1, MLKL or RIPK3 expression in the cell or tissue or through destabilisation of RIPK1, MLKL or RIPK3 protein within the cell or tissue. The presence of a lower RIPK1, MLKL or RIPK3 activity or a decreased amount of RIPK1, MLKL or RIPK3 within the cell or tissue in the presence of the test agent indicates that the test agent may be a suitable antagonist of RIPK1, MLKL or RIPK3 for use in accordance with the present invention in the treatment of an individual having liver failure such as ALF and ACLF or suffering from aberrant necroptosis.

In one embodiment, such a cell based assay may be carried out in vitro or ex vivo on cells or tissue deriving from the patient to be treated. It may therefore be determined whether or not the test agent is capable of decreasing the activity or amount of RIPK1, MLKL or RIPK3 in the cells or tissue of that subject. For example, such a method may be carried out on a sample of cells or tissue from the liver of the patient.

A method of the invention may use a cell-free assay. For example, the RIPK1, MLKL or RIPK3 may be present in a cell-free environment. A suitable cell-free assay may be carried out in a cell extract. For example, the contacting steps of the methods of the invention may be carried out in extracts obtained from cells that may express, produce or otherwise contain RIPK1, MLKL or RIPK3 and/or a test agent. A cell-free system comprising RIPK1, MLKL or RIPK3 may be incubated with the other components of the methods of the invention such a test agent.

In such a cell-free method, the amount of RIPK1, MLKL or RIPK3 may be assessed in the presence or absence of a test agent in order to determine whether the agent is altering the amount of RIPK1, MLKL or RIPK3 in the cell or tissue, such as through destabilisation of RIPK1, MLKL or RIPK3 protein. In either case, the presence of a lower RIPK1, MLKL or RIPK3 activity or a decreased amount of RIPK1, MLKL or RIPK3 in the presence of the test agent indicates that the test agent may be a suitable antagonist of RIPK1, MLKL or RIPK3 for use in accordance with the present invention in the treatment of an individual having ACLF or suffering from aberrant necroptosis.

The contacting step(s) of the method of the invention may comprise incubation of the various components. Such incubations may be performed at any suitable temperature, typically between 4° C. and 40° C. Incubation periods may be selected for optimum activity, but may also be optimized to facilitate rapid high-throughput screening. Following the contact and optional incubation steps, the subject methods may further include a washing step to remove unbound components, where such a washing step is generally employed when required to remove label that would give rise to a background signal during detection, such as radioactive or fluorescently labelled non-specifically bound components.

Incubation in cell or cell-free assay systems may be performed in a microtiter plate (e.g. a 96-well plate or other microwell plate). Further, incubation may be performed in an automated fashion (e.g. for high-throughput screening).

A screening method of the invention may be carried out in vivo. For example, a screening method may be carried out in an animal model. In such an in vivo model, the effects of a test agent may be assessed in the liver, or in other organs such as the kidney or heart. Preferably, the animal is a non-human animal such as a rat or a mouse. The screening method of the present invention may comprise the step of administering a test agent to a bile duct ligated rat or another model of ACLF such as that caused by administration of carbon tetrachloride and determining whether the presence of the test agent leads to a decrease in the amount or activity of RIPK1, MLKL or RIPK3 in the immune system, liver, kidney, brain or other organs of the rodent.

Such a model may be used to assess the in vivo effects of a test agent. For example, such a model may be used to assess whether the test agent is capable of decreasing the activity or amount of RIPK1, MLKL or RIPK3 in vivo. In such a method, the amount of RIPK1, MLKL or RIPK3 may be assessed and/or the activity of RIPK1, MLKL or RIPK3 may be assessed.

An in vivo model may also be used to determine whether the test agent has any unwanted side effects. For example, a method of the invention may compare the effects of a test agent on RIPK1, MLKL or RIPK3 with its effects on other receptors in order to determine whether the test agent is specific.

In an in vivo model as described herein, or an in vitro model such as a cell-based or cell-free assay model as described herein, the effects of a test agent on RIPK1, MLKL or RIPK3 may be compared with the effects of the same agent on other related proteins. As discussed above, a preferred RIPK1, MLKL or RIPK3 antagonist for use in a method of treatment as described herein may be an agent that antagonises RIPK1, MLKL or RIPK3, but that does not antagonise other related proteins. The screening methods of the invention may thus include an additional step of assessing whether the test agent has any effect on the activity or amount of one or more other related proteins that are not RIPK1, MLKL or RIPK3. In such a method, a test agent may be identified as a suitable RIPK1, MLKL or RIPK3 antagonist if it is found to decrease the activity or amount of RIPK1, MLKL or RIPK3, but not to decrease, not to significantly decrease, not to significantly decrease, not to alter, or not to significantly alter, the activity or amount of one or more other related proteins in the same assay.

Where the assay is carried out in vivo, for example in a bile duct ligated rat model as described herein, such a method may comprise comparing the amount or activity of RIPK1, MLKL or RIPK3 in the immune system, liver, kidney or other organs of the test animal in the presence or absence of the test agent. An observation that the level or activity of RIPK1, MLKL or RIPK3 is decreased in the immune system, liver, kidney or other organs of animals treated with the test agent suggests that the test agent may be a suitable antagonist of RIPK1, MLKL or RIPK3. A further finding that treatment with the same test agent does not significantly decrease or alter the levels or activity of one or more other related proteins, may further indicate that the test agent is a suitable specific antagonist of RIPK1, MLKL or RIPK3 that may be used in the methods of treatment described herein.

In the screening methods described herein, the presence of a lower RIPK1, MLKL or RIPK3 activity or a decreased amount of RIPK1, MLKL or RIPK3 in the presence of the test agent indicates that the test agent may be a suitable antagonist of RIPK1, MLKL or RIPK3 for use in accordance with the present invention to treat an individual having ACLF or suffering from aberrant necroptosis.

A test agent that is an antagonist of RIPK1, MLKL or RIPK3 may result in a decrease in RIPK1, MLKL or RIPK3 activity or levels of at least 5%, at least 10%, at least 25%, at least 50%, at least 60%, at least 75%, or at least 85% or more in the presence of the test agent compared to in the absence of the test agent. A test agent that is an antagonist of RIPK1, MLKL or RIPK3 may result in a decrease in RIPK1, MLKL or RIPK3 activity or levels such that the activity or level of RIPK1, MLKL or RIPK3 is no longer detectable in the presence of the test agent. Such a decrease may be seen in the sample being tested or, for example where the method is carried out in an animal model, in particular tissue from the animal such as in the liver.

A test agent that is an antagonist of RIPK1, MLKL or RIPK3 may be a specific or selective antagonist of RIPK1, MLKL or RIPK3 as described above. For example, the agent may have an effect on other related proteins, such as antagonism of the activity, signalling or expression of one or more other related proteins, that is less than 25%, less than 20%, less than 15%, less than 10%, less than 5%, less than 1%, or less than 0.1% the effect of that agent on the activity, signalling or expression of RIPK1, MLKL or RIPK3.

Levels or amounts of RIPK1, MLKL or RIPK3 may be measured by assessing expression of the RIPK1, MLKL or RIPK3 gene. Gene expression may be assessed by looking at mRNA production or levels or at protein production or plasma/serum concentrations. Expression products such as mRNA and proteins may be identified or quantified by methods known in the art. Such methods may utilise hybridisation to specifically identify the mRNA of interest. For example such methods may involve PCR or real-time PCR approaches. Methods to identify or quantify a protein of interest may involve the use of antibodies that bind that protein. For example, such methods may involve western blotting. Regulation of RIPK1, MLKL or RIPK3 gene expression may be compared in the presence and absence of a test agent. Thus test agents can be identified that decrease RIPK1, MLKL or RIPK3 gene expression compared to the level seen in the absence of the test agent. Such test agents may be suitable antagonists of RIPK1, MLKL or RIPK3 in accordance with the invention.

The screening methods may assess the activity of RIPK1, MLKL or RIPK3. For example, such a method may be carried out using peripheral blood mononuclear cells. Such cells will produce cytokines such as TNFα and NFkβ on response to stimulation with, for example, lipopolysaccharide (LPS). A screening method may therefore comprise combining peripheral blood mononuclear cells with the test agent or a vehicle and adding LPS. The cells may then be incubated for an amount of time (e.g. 24 hours) to allow the production of inflammatory molecules such as cytokines. The level of cytokines such as TNFα and NFkβ produced by the cells in that time period can then be assessed. If the test agent has anti-RIPK1, MLKL or RIPK3 properties, then the production of such cytokines or NFkβ should be reduced compared to the vehicle-treated cells.

Pharmaceutical Formulations

A suitable RIPK1, MLKL or RIPK3 antagonist as described herein is typically formulated for administration with a pharmaceutically acceptable carrier or diluent. The antagonist may be any antagonist as defined herein including any antagonist identified by a screening method of the invention. The antagonist may thus be formulated as a medicament with a standard pharmaceutically acceptable carrier(s) and/or excipient(s) as is routine in the pharmaceutical art. The exact nature of the formulation will depend upon several factors including the desired route of administration. Typically, the antagonist may be formulated for oral, intravenous, intragastric, intravascular or intraperitoneal administration.

The pharmaceutical carrier or diluent may be, for example, an isotonic solution such as physiological saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with ornithine and at least one of phenylacetate and phenylbutyrate, a pharmaceutically acceptable carrier, e.g. sterile water, olive oil, ethyl oleate, glycols, e.g. propylene glycol, and if desired, a suitable amount of lidocaine hydrochloride.

Where the antagonist to be administered is a nucleic acid molecule, for example where the antagonist is in the form of an expression vector, certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules.

A pharmaceutical formulation in accordance with the present invention may further comprise one or more additional therapeutic agents. For example, the formulation may comprise one or more RIPK1, MLKL or RIPK3 antagonists as defined herein. The formulation may comprise one or more RIPK1, MLKL or RIPK3 antagonists as described here and also one or more additional therapeutic agents. Preferably the additional therapeutic agent(s) are agents which will assist in the treatment or prophylaxis of the individual to be treated. For example, one or more agents that are effective at treating liver disease may be administered as part of a formulation as described herein. One or more agents that are effective at treating an underlying liver condition or symptom thereof in the patient may be administered as part of a formulation as described herein.

Treatment

The present invention provides methods for the treatment of individuals having liver failure such as ALF and ACLF or suffering from aberrant necroptosis, particularly for the treatment or prevention of symptoms and conditions associated with or resulting from liver failure such as ALF and ACLF or aberrant necroptosis.

Accordingly, the invention provides a method of treating an individual having liver failure such as ALF and ACLF comprising administering to said subject an antagonist of the necroptotic signalling cascade. Similarly, an antagonist of the necroptotic signalling cascade may be provided for use in a method of treating an individual having liver failure such as ALF and ACLF. Also provided is the use of an antagonist of the necroptotic signalling cascade in the manufacture of a medicament for use in the treatment of an individual having liver failure such as ALF and ACLF.

Accordingly, the invention provides a method of treating an individual having liver failure such as ALF and ACLF comprising administering to said subject an antagonist of RIPK1, MLKL or RIPK3. Similarly, an antagonist of RIPK1, MLKL or RIPK3 may be provided for use in a method of treating an individual having liver failure such as ALF and ACLF. Also provided is the use of an antagonist of RIPK1, MLKL or RIPK3 in the manufacture of a medicament for use in the treatment of an individual having liver failure such as ALF and ACLF.

Accordingly, the invention provides a method of treating an individual suffering from aberrant necroptosis comprising administering to said subject an antagonist of RIPK1, MLKL or RIPK3. Similarly, an antagonist of RIPK1, MLKL or RIPK3 may be provided for use in a method of treating an individual suffering from aberrant necroptosis. Also provided is the use of an antagonist of RIPK1, MLKL or RIPK3 in the manufacture of a medicament for use in the treatment of an individual suffering from aberrant necroptosis.

The antagonist may be any antagonist as described herein including any antagonist identified by a screening method of the invention. The antagonist may be provided in a formulation as described herein. An antagonist of RIPK1, MLKL or RIPK3 as described herein is thus administered to a subject in order to treat or prevent liver failure such as ALF and ACLF or aberrant necroptosis, or particular symptoms or conditions associated with liver failure such as ALF and ACLF or aberrant necroptosis in the subject. An antagonist of RIPK1, MLKL or RIPK3 as described herein can thus be administered to improve the condition of a subject, for example a subject suffering from liver failure such as ALF and ACLF or aberrant necroptosis. An antagonist of RIPK1, MLKL or RIPK3 as described herein may be administered to alleviate the symptoms of a subject, for example the symptoms associated with liver failure such as ALF and ACLF or aberrant necroptosis.

An antagonist of RIPK1, MLKL or RIPK3 as described herein may be administered to alleviate the symptoms of a subject, for example the symptoms associated with aberrant necroptosis.

An antagonist of RIPK1, MLKL or RIPK3 as described herein may be administered to combat or delay the onset of liver failure such as ALF and ACLF or any symptom associated therewith. The invention can therefore prevent the medical consequences of liver failure such as ALF and ACLF. Use of an antagonist of RIPK1, MLKL or RIPK3 as described herein may thus extend the life of a patient with liver failure such as ALF and ACLF.

The treatment of liver failure such as ALF and ACLF, refers to the treatment of an individual having or at risk of having liver failure such as ALF and ACLF. The individual may also be suffering from chronic liver disease such as cirrhosis or alcoholic cirrhosis. The patient may be suffering from liver disease or cirrhosis associated with or caused by an infection such as a hepatitis virus infection such as hepatitis C virus infection. The patient may be suffering from liver disease or cirrhosis associated with or caused by treatment with a hepatotoxin such as acetaminophen (paracetamol). The methods described herein may be used in the treatment of any such disease.

The individual may be suffering from one or more symptoms or conditions caused by or associated with liver failure such as ALF and ACLF. Any one or more of these conditions or symptoms may be treated in accordance with the present invention. For example, the individual may be suffering from, or at risk of, one or more of the following as a result of their liver failure such as ALF and ACLF: renal dysfunction; renal failure; HRS; increased plasma creatinine; brain dysfunction and brain swelling increased plasma ammonia; increased liver enzyme concentrations (such as increased concentrations of ALT and/or AST in the liver); increased inflammation, injury and/or dysfunction in the liver and/or kidney and/or brain and/or blood circulation; liver tissue damage resulting from liver failure, such as resulting from acetaminophen (APAP) toxicity. The individual may be suffering from, or at risk of, acute liver failure, alcoholic hepatitis and/or reperfusion injury of the liver. Those conditions may result from the liver failure such as ALF and ACLF of the individual. The methods and uses described herein may be of utility in the treatment or prevention of any one or more of these symptoms or conditions, particularly, in an individual suffering from liver failure such as ALF and ACLF.

In particular, the methods described herein may be used in the treatment of a patient having liver failure such as ALF and ACLF. For example, the patient may have or be at risk or renal failure. The liver failure such as ALF and ACLF may result from an infection and/or inflammation. The liver failure such as ALF and ACLF may result from exposure to a hepatotoxin such as acetaminophen (paracetamol) such as exposure to a high level of the hepatotoxin, such as an overdose with paracetamol. The methods described herein may be used to treat or prevent any of these conditions or symptoms, particularly to treat or prevent the ACLF from such a condition or exposure.

As described herein, the antagonist of RIPK1, MLKL or RIPK3 may lead to decreased expression and/or decreased levels of RIPK1, MLKL or RIPK3 in the liver of the subject. For example, the antagonist may be an agent that inhibits transcription of RIPK1, MLKL or RIPK3 in cells of the subject.

As described herein, the antagonist of RIPK1, MLKL or RIPK3 may lead to decreased activity of RIPK1, MLKL or RIPK3 in the liver of the individual.

The subject is treated with an antagonist of RIPK1, MLKL or RIPK3 as described herein. As described above, the antagonist of RIPK1, MLKL or RIPK3 may be administered alone or in the form of a pharmaceutical formulation. The formulation may comprise one or more antagonists of RIPK1, MLKL or RIPK3 and may comprise one or more additional therapeutic or prophylactic agents.

Two or more different RIPK1, MLKL or RIPK3 antagonists as described herein may be used in combination to treat a subject. The two or more antagonists may be administered together, in a single formulation, at the same time, in two or more separate formulations, or separately or sequentially as part of a combined administration regimen.

An antagonist of the invention may be administered in combination with another agent known to be useful in the treatment or prevention of liver failure such as ALF and ACLF. The antagonists may be administered together, in a single formulation, at the same time, in two or more separate formulations, or separately or sequentially as part of a combined administration regimen.

An antagonist or formulation of the invention may be administered by any suitable route. Preferably it is administered by oral, intravenous, intragastric, intraperitoneal or intravascular routes. The antagonist or formulation may be administered directly to the liver of the subject.

The antagonist is administered in a therapeutically effective amount. A suitable dose of an antagonist of the invention can be determined according to various parameters such as the age, weight and condition of the subject to be treated; the type and severity of the liver disease; the route of administration; and the required regimen. A suitable dose can be determined for an individual antagonist. For example, for some antagonists a typical dose may be in the order of from 0.1 mg/kg/day to 30 g/kg/day. A physician will be able to determine the required dosage of antagonist and for any particular subject.

The present invention is broadly applicable to therapeutic methods and is relevant to the development of prophylactic and/or therapeutic treatments. It is to be appreciated that all references herein to treatment include curative, palliative and prophylactic treatment.

Prophylaxis or therapy includes but is not limited to eliciting an effective decrease in RIPK1, MLKL or RIPK3 amount, function or activity in order to cause a reduction in one or more symptoms or conditions associated with, or resulting from liver failure such as ALF and ACLF or aberrant necroptosis. The symptoms or conditions may be, for example, any of those discussed above. For example, prophylaxis or therapy may result in: reduced symptoms of renal dysfunction, prevention or reduced symptoms of liver failure, reduced levels of plasma creatinine, plasma ammonia, liver enzyme concentrations (such as reduced concentrations of ALT and/or AST in the liver), reduced inflammation in the liver and/or kidney and/or brain and/or blood circulation, and or a reduction in liver tissue damage resulting from liver failure, such as resulting from acetaminophen (APAP) toxicity. Prophylaxis or therapy may result in the maintenance of a particular level of renal dysfunction, renal failure, plasma creatinine, brain dysfunction and/or brain swelling, plasma ammonia, liver enzyme concentrations (such as concentrations of ALT and/or AST in the liver), inflammation in the liver and/or kidney and/or brain and/or blood circulation, and or liver tissue damage resulting from liver failure, such as resulting from acetaminophen (APAP) toxicity, in a patient where such symptoms have been increasing or are expected to increase as a result of the liver failure such as ALF and ACLF. Prophylaxis or therapy may result in such changes in symptoms or conditions in such an individual changing at a reduced rate compared to the changes that would have been seen or would have been expected in the absence of such treatment.

Prophylaxis or therapy may have similar effects in relation to any of the symptoms or consequences of liver failure such as ALF and ACLF or aberrant necroptosis described herein. That is, treatment in accordance with the present invention may lead to a lessening in the severity of such symptoms or consequences, maintenance of an existing level of such symptoms or consequences or a slowing or reduction in the worsening of such symptoms or consequences.

Patients to be Treated

The present invention relates to the treatment or prevention of liver failure such as ALF and ACLF or aberrant necroptosis in individuals in need thereof. An individual to be treated in accordance with the present invention may therefore have liver failure such as ALF and ACLF or may be at increased risk of liver failure such as ALF and ACLF. For example, the subject may have liver failure. The subject may have immune dysfunction or failure, systemic inflammation, renal failure or brain dysfunction and/or brain swelling.

Methods for diagnosing liver failure, immune dysfunction, renal dysfunction, brain dysfunction, brain swelling or immune failure are well known in the art and in particular to clinicians and veterinarians in the field. For example, renal dysfunction is characterised by a reduction or loss of renal function, which may be assessed by monitoring urine volume, or sodium concentration and osmolality of the urine. Hepatorenal syndrome is also associated with a reduction in renal blood flow. Preferably, the subject will have been diagnosed as having liver failure for example by a medical or veterinarian professional. The subject may display one or more symptoms associated with liver failure, renal dysfunction or renal failure.

Methods for diagnosing liver failure such as ALF and ACLF are well known in the art and in particular to clinicians and veterinarians in the field. ACLF is diagnosed by use of the Chronic Liver Failure (CLiF) Consortium criteria, NACSELD criteria or APASL criteria. Previously validated scores to assess disease severity include Child- Pugh (CP) classification, Model for End Stage Liver Disease (MELD) and the CLiF Consortium Acute Decompensation (CLIF-C AD) score.

The individual to be treated may have increased expression of RIPK1, MLKL or RIPK3 in the liver compared with a healthy individual, such as an individual not having liver failure such as ALF and ACLF. The individual to be treated may have increased serum or plasma RIPK3 compared with a healthy individual, such as an individual not having liver failure such as ALF and ACLF.

A patient may be identified as being suitable for treatment as described herein by a method comprising measuring the level of RIPK3 in the serum or plasma of the patient and comparing the level of serum or plasma RIPK3 with the level of serum or plasma RIPK3 from a healthy individual, such as an individual not having liver failure such as ALF and ACLF. In such a method, an increased level of serum or plasma RIPK3 indicates that the patient may be suitable for treatment according to the present invention.

The individual to be treated may have been diagnosed as suffering from ACLF, or one or more symptoms or conditions as described herein that may be associated with liver failure such as ALF and ACLF, for example by any of these methods. The individual to be treated may have been diagnosed as being at risk of liver failure such as ALF and ACLF. For example, the individual may have been diagnosed with one or more symptoms that are associated with liver failure, cirrhosis, renal failure and/or renal failure. For example, the individual to be treated may have liver cirrhosis, alcoholic hepatitis, idiopathic non-cirrhotic portal hypertension, congenital hepatic fibrosis, partial nodular transformation, Budd-Chiari syndrome, portal vein thrombosis, right heart failure or schistosomiasis infection.

The subject to be treated may be any individual which is susceptible to liver failure such as ALF and ACLF. The subject may be male or female. Women may be more susceptible to the adverse effects of alcohol than men. Women can develop chronic liver disease in a shorter time frame and from smaller amounts of alcohol than men.

The subject to be treated may be a human. The subject to be treated may be a non-human animal. The subject to be treated may be a farm animal for example, a cow or bull, sheep, pig, ox, goat or horse or may be a domestic animal such as a dog or cat. The subject may or may not be an animal model for liver disease. The animal may be any age, but will often be a mature adult subject.

Biomarkers for Diagnosis

As explained above, the present invention relates to the treatment of patients suffering from liver failure such as ALF and ACLF. As reported in the examples, the Inventors have unexpectedly found that there are detectable changes in RIPK3 levels in patients and in an animal model of liver failure such as ALF and ACLF.

Accordingly, a method is provided for the detection or prediction of liver failure such as ALF and ACLF in an individual as described above. The individual may be any of the individuals as described above under the heading "patients to be treated".

For example, a method of diagnosing liver failure such as ALF and ACLF or of predicting liver failure such as ALF and ACLF in a patient may comprise the steps of (a) detecting the expression or expression pattern of RIPK1, MLKL or RIPK3 in the serum or plasma of the patient and (b) comparing the expression level or expression pattern of (a) with a control level or pattern of RIPK1, MLKL or RIPK3 expression based on the expression of RIPK1, MLKL or RIPK3 found in the serum or plasma of a healthy individual such as an individual not suffering from liver failure such as ALF and ACLF. The method may comprise measuring the level or expression of RIPK1, MLKL or RIPK3 in the serum or plasma of the patient and in the serum or plasma of a control individual such as a healthy individual described above and comparing the level or expression of RIPK1, MLKL or RIPK3 in the two samples. The method may comprise measuring the level or expression of RIPK1, MLKL or RIPK3 in the serum or plasma of the patient and comparing that level with a known control level or expression pattern based on earlier measurements from a control individual or group of control individuals as described above.

For example, a method of diagnosing liver failure such as ALF and ACLF or of predicting liver failure such as ALF and ACLF in a patient may comprise the steps of (a) detecting the expression or expression pattern of RIPK3 in the serum or plasma of the patient and (b) comparing the expression level or expression pattern of (a) with a control level or pattern of RIPK3 expression based on the expression of RIPK3 found in the serum or plasma of a healthy individual such as an individual not suffering from ACLF. The method may comprise measuring the level or expression of RIPK3 in the serum or plasma of the patient and in the serum or plasma of a control individual such as a healthy individual described above and comparing the level or expression of RIPK3 in the two samples. The method may comprise measuring the level or expression of RIPK3 in the serum or plasma of the patient and comparing that level with a known control level or expression pattern based on earlier measurements from a control individual or group of control individuals as described above.

In such methods, an increased level of RIPK3 expression in the serum or plasma of the patient compared with the control level indicates that the patient has an increased likelihood of, an increased risk of or that the individual is already suffering from, liver failure such as ALF and ACLF. An increased level of RIPK3 expression in the serum or plasma of the patient compared with the control level indicates that the patient has an increased likelihood of, an increased risk of or that the individual is already suffering from, liver failure such as ALF and ACLF.

Methods are also provided which utilise the findings of the present inventors that serum or plasma RIPK1, MLKL or RIPK3 levels are increased in liver failure such as ALF and ACLF.

Methods are also provided which utilise the findings of the present inventors that serum or plasma RIPK3 levels are increased in liver failure such as ALF and ACLF.

For example, a method of diagnosing liver failure such as ALF and ACLF or of predicting liver failure such as ALF and ACLF in a patient may comprise the steps of (a) measuring the level of RIPK3 in the serum or plasma of the patient and (b) comparing the level of (a) with a control level of RIPK3 based on the level of RIPK3 found in the serum or plasma of a healthy individual such as an individual not suffering from liver failure such as ALF and ACLF. The method may comprise measuring the level of RIPK3 in a serum or plasma sample from the patient and in a serum or plasma sample from a control individual such as a healthy individual described above and comparing the levels of RIPK3 in the two samples. The method may comprise measuring the level of RIPK3 in a serum or plasma sample from the patient and comparing that level with a known control level based on earlier measurements from a control individual or group of control individuals as described above. In such methods, an increased level of serum or plasma RIPK3 in the patient compared with the control level indicates that the patient has an increased likelihood of, an increased risk of or that the individual is already suffering from, liver failure such as ALF and ACLF.

A further method may be used to predict whether the patient is likely to suffer from liver failure such as ALF and ACLF. This information may be used by a clinician to determine how the patient is treated and their condition monitored.

Such a method may comprise the steps of (a) measuring the level of RIPK1, MLKL or RIPK3 in the serum or plasma of the patient and (b) comparing the level of (a) with a known level of RIPK1, MLKL or RIPK3 based on the level of RIPK1, MLKL or RIPK3 found in the serum or plasma of a control individual suffering from liver disease who did not go on to suffer from liver failure such as ALF and ACLF. The method may comprise measuring the level of RIPK1, MLKL or RIPK3 in a serum or plasma sample from the patient and in a serum or plasma sample from the control individual and comparing the levels of RIPK1, MLKL or RIPK3 in the two samples. The method may comprise measuring the level of RIPK1, MLKL or RIPK3 in a serum or plasma sample from the patient and comparing that level with a known control level based on earlier measurements from a control individual as described above. In such methods, an increased level of serum or plasma RIPK1, MLKL or RIPK3 in the patient compared with the control level indicates that the patient has an increased likelihood of, an increased risk of or the individual is already suffering from, liver failure such as ALF and ACLF.

Such a method may comprise the steps of (a) measuring the level of RIPK3 in the serum or plasma of the patient and (b) comparing the level of (a) with a known level of RIPK3 based on the level of RIPK3 found in the serum or plasma of a control individual suffering from liver disease who did not go on to suffer from liver failure such as ALF and ACLF. The method may comprise measuring the level of RIPK3 in a serum or plasma sample from the patient and in a serum or plasma sample from the control individual and comparing the levels of RIPK3 in the two samples. The method may comprise measuring the level of RIPK3 in a serum or plasma sample from the patient and comparing that level with a known control level based on earlier measurements from a control individual as described above. In such methods, an increased level of serum or plasma RIPK3 in the patient compared with the control level indicates that the patient has an increased likelihood of, an increased risk of or the individual is already suffering from, liver failure such as ALF and ACLF.

For example, an increased level of serum or plasma RIPK3 or of RIPK3 expression in these methods when compared with a control level may be a statistically significant increase in serum or plasma RIPK3 concentration or RIPK3 expression level. An increased level of serum or plasma RIPK3 or RIPK3 expression in these methods may be an increase of at least 15%, at least 25%, at least 50%, at least 75%, at least 100%, at least 200%, at least 300% or more when compared to a suitable control. The control may be the serum or plasma RIPK3 level from a single control individual or may be an average value obtained from a group of control individuals.

The method may comprise testing a sample from the individual for the presence of one or more markers of liver failure such as ALF and ACLF. The presence of such markers in the sample from the individual may indicate that the individual is suffering from liver failure such as ALF and ACLF, or is at increased risk of, liver failure such as ALF and ACLF. The markers may be markers associated with damage to the glomeruli or the renal tubules. For example, if the sample is a sample of serum, the sample may be tested for the presence of one or more markers selected from (a) IL-6 (interleukin-6) and/or IL-10 (interleukin-10) and/or TNFα, (b) MMP-9 (matrix metalloproteinase 9), (c) NAG (N-Acetylglucosamine), (d) myeloperoxidase and (e) glutathione S transferase. Any combination of these markers may be used, optionally with additional markers not specifically mentioned here. Preferably more than one of the markers mentioned above is assessed, such as at least two, at least three, at least four or at least five of these markers.

An individual who has been identified by any such method as having, or being at risk of, liver failure such as ALF and ACLF, may then be provided with appropriate therapeutic or preventative treatment for that condition. This may allow suitable treatment to be provided earlier than would have been possible when detecting liver failure such as ALF and ACLF using known methods. An individual who has been identified by any of these methods as having, or being at risk of, liver failure such as ALF and ACLF, may then be treated by any of the therapeutic or prophylactic methods described herein.

A method may also be provided in order to identify further suitable biomarkers that could be used in the detection methods described herein. This may involve comparing samples obtained from individuals having liver failure such as ALF and ACLF with samples obtained from a normal individual or an individual not having liver failure such as ALF and ACLF. The method may involve identifying markers that can distinguish between a sample from an individual having liver failure such as ALF and ACLF and a sample from a normal individual.

A suitable marker may be identified using samples from the organism of interest, such as samples from human individuals. A suitable marker may be identified using samples from an animal model, such as the bile duct ligated (BDL) rat or carbon tetrachloride treated mouse. Such samples may be compared with samples from a normal or sham treated animal.

The sample may be any suitable sample that can be readily retrieved from a suitable individual, such as a sample of urine, plasma, serum or blood. The marker may be a protein or other molecule that is present in one of the samples, but not in the other sample, or that is present in significantly different amounts in the two samples, such that the samples can be distinguished on the basis of that molecule. A marker that is identified in this way as being capable of distinguishing between the two types of sample may be used in a method as described above in order to determine whether or not an individual, particularly an individual having liver disease, has, or is at risk of, liver failure such as ALF and ACLF. This may be achieved by comparing the presence, absence or amount of the marker in a sample obtained from the individual of interest with the known presence, absence or amount of that marker in known samples, and thereby correlating the sample from the individual with either a control sample from a normal individual or a diseased sample from an individual with liver failure such as ALF and ACLF.

EXAMPLES

Methods

Patient Population

The samples and data of patients with AD and ACLF were obtained from the prospective multicentre observational DASIMAR study (NCT01071746). Samples and data from healthy volunteers and those with stable cirrhosis were obtained from archived bio-banked material at the Royal Free hospital. Additionally, liver sections from patients with alcoholic hepatitis with or without ACLF were obtained from the histology department of the Royal Free Hospital in London (UCL Biobank Ethical Review Committee approval number NC.2017.10) All the samples were collected with informed consent from the patients and the principles of good clinical practice and the Declaration of Helsinki, 1951 were followed closely throughout.

Quantification of Plasma RIPK3 Levels

All blood samples were centrifuged at 2000 rpm for 10 minutes and the supernatants were stored at −80 within 4 hours of collection. Plasma RIPK3 levels were then measured in baseline EDTA samples by ELISA [Human Receptor-Interacting Serine/Threonine-Protein Kinase 3 (RIPK3) ELISA Kit (Cusabio, USA)]. The optical density was determined using a microplate reader set to 450 nm (BMG Labtech FLUOstar Omega).

ACLF Animal Model

The animal model of ACLF utilised in this study was developed using a well-characterized rodent model of advanced fibrosis induced by bile duct ligation (BDL) with ACLF induced in this model by infusion of LPS. Bile duct ligation, housing, and care of the animals were performed as previously described. Four groups of adult male Sprague-Dawley rats were studied (n=4-8 in each group). The animals were studied 4 weeks after either sham-operation or BDL. The animals in each group were terminated 3-h after administration of LPS (*Klebsiella pneumoniae*) (0.3 mg/kg/hr, intravenously) or saline under terminal anaesthesia.

*Klebsiella pneumoniae* LPS (Sigma, UK) was dissolved in saline at a final concentration of 1 mg/ml. This stock was then diluted 1:100 (0.01 mg/ml) in saline before injection into the animals.

Necrostatin 1 (Nec-1, Calbiochem, Sigma Aldrich, UK) was prepared as follows. Nec-1 was redissolved in N-2 methyl-pyrrolidone (NMP) to make a 200 mg/ml stock solution which was then further diluted to an intermediate concentration of 40 mg/ml in NMP. The 40 mg/ml solution was finally diluted to a working concentration of 1 mg/ml in a solution of 30% (2-hydroxypropyl) β-cyclodextrin (Sigma, Cat No H107)/0.5% Citric acid.

The groups were as follows:
1. Sham operated controls administered saline
2. BDL animals administered saline
3. BDL animals administered LPS
4. BDL animals administered LPS and Nec-1; This group of BDL rats received an i.p. injection of 3.3 mg/kg Nec-1 followed, by an i.p injection of LPS, 3 hr later.

Animals were sacrificed 3 hours after LPS.

Blood was withdrawn from the carotid line and immediately placed in heparin or EDTA-containing tubes (until full exsanguination), centrifuged (3,500 rpm for 10 min at 4° C.) and the plasma was stored at −80° C. for later use in biochemistry and RIPK3 quantification [Rat RIPK3 (Receptor-interacting serine/threonineprotein kinase) ELISA kit, Cat. No. ER0446, Wuhan Fine Biological Technology Co., Ltd., China]. Organs were harvested and either fixed in formalin for histological assessment or snap frozen.

Caspase Assays

Liver Caspase 3/7 and 8 activities were measured using Caspase-Glo assay kits (Promega). Briefly, cytosolic extracts from liver tissue were obtained by homogenisation in hypotonic extraction buffer [10 mM HEPES, 0.5% Triton X-100, 2 mM DTT, protease inhibitor cocktail (Sigma)] using a TissueLyser LT sytem (Qiagen, UK). After homogenisation the extracts were centrifuged for 10 min at 10000 rpm (at 4° C.). After quantification using BCA™ Protein Assay Kit (Pierce, UK), protein concentrations of supernatant were adjusted to 1 mg/ml with extraction buffer and stored at −80° C. Diluted lysates (10 µg/ml) were mixed with an equal volume of Caspase-Glo reagents (100 µl each) in white-walled 96-well plate and incubated at room temperature for 1 hour. Luminescence was measured using a plate-reading luminometer (FLUOstar Omega, BMG Labtech, UK).

Immunohistochemistry

Liver sections of patients with alcoholic hepatitis with and without ACLF and of Sham, BDL and BDL+LPS treated rats were stained for expression of necroptosis markers. Briefly, single-labeling immunohistochemistry was performed according to the avidin biotinylated-HRP complex (ABC) method using an R.T.U. VECTASTAIN Universal® ABC Kit (Anti-Mouse IgG/Rabbit IgG) kit (Vector Laboratories, Burlingame, Calif.) as per manufacturer's instructions. Sections were blocked for 30 min at room temperature in a blocking solution containing 3% normal goat serum (NGS) in TBS and incubated overnight at 4° C. with primary antibodies specific for RIPK1 (GTX31389, GeneTex—Dilution 1:400), RIPK3 (GTX107574, GeneTex—Dilution 1:500) and pMLKL (S358) (human sections only) (ab187091, Abcam—Dilution 1: 250) in TBS containing 0.05% Triton X-100 and 0.5% NGS. The following day, sections were rinsed in TBS (2×10 min) and incubated for 45 min at RT in biotinylated secondary antibodies, followed by 45 min in ABC solution (prepared according to the manufacturer's instructions). Visualization of bound peroxidase was achieved by using the DAB Peroxidase Substrate Kit (SK-4100, Vector Lab, USA). Sections were counterstained with haemotoxylin. Specimens were imaged with a Carl Zeiss Axiovert 200M microscope equipped with a Plan-Neofluar 10x/0.3 objective and an AxioCamMR2 camera system with Axiovision software (Carl Zeiss Inc., Germany).

In Situ Detection of Cell Death by the TUNEL Assay

Terminal deoxynucleotidyl transferase biotin-dUTP nick end labeling (TUNEL) staining of deparaffinised and proteinase K-treated liver and kidney sections was performed using the In-Situ Cell Death Detection kit, POD (Roche, UK) as per manufacturer's protocol. Specimens were imaged with a Carl Zeiss Axio Scope. A1 microscope equipment with N-Achroplan 10x/0.25 Ph1 and 40x/0.65 Ph2 objectives and Axio Cam Mrc5 (Carl Zeiss Inc., Germany). Quantitative analysis of immunohistochemistry positive area was assessed by measuring optical density using FIJI Image J software.

Statistical Analysis

Human data are expressed as the mean standard deviation for normally distributed continuous variables, median and interquartile range (IQR) for not normally distributed continuous variables, and frequencies and percentages for categorical variables. Animal data were expressed as the mean standard error of mean. Continuous variables were analyzed using Student's t test, Mann-Whitney U test, or Kruskal-Wallis test, as appropriate. Categorical variables were analyzed by Fisher's exact test. p value of less than 0.05 was considered to be significant.

Example 1

Patient Characteristics (Table 1)

One hundred and forty cirrhotic patients from the DASIMAR study cohort with AD were enrolled. The characteristics of this group can be seen in table 1. Of this number, 83 patients presented with no ACLF, 23 with ACLF grade 1 and 34 with ACLF grade 2 or 3. 18 of the no ACLF patients progressed to ACLF whilst inpatients. Additional 42 patients with stable cirrhosis (SC) and 21 healthy volunteers (HV) were also studied.

As would be expected from the previously published literature, patients with ACLF presented with significantly worse biochemical and haematological parameters and associated clinical scores, higher rates of organ failure and the presence of ACLF was associated with an increased 3-month mortality.

TABLE 1

Baseline characteristics stratified by presence or absence of ACLF at enrolment

|  | No ACLF (n = 59) | ACLF (n = 47) | P value |
|---|---|---|---|
| Age (years) | 51 (45-65) | 49 (41-54) | 0.054 |
| Male (n, %) | 32 (54.2) | 30 (63.8) | 0.331 |
| Etiology (n, %) | | | |
| Alcohol | 31 (52.5) | 34 (72.3) | 0.046 |
| Alcohol + HCV | 8 (13.6) | 3 (6.4) | 0.339 |
| HCV | 5 (8.5) | 2 (4.3) | 0.459 |
| Non-alcoholic steatohepatitis | 6 (10.2) | 2 (2.1) | 0.130 |
| Other | 9 (15.3) | 7 (14.9) | >0.999 |
| Active alcoholism at enrollment (n, %) | 41 (69.5) | 37 (78.7) | 0.376 |
| Ascites (n, %) | 28 (47.5) | 31 (66.0) | 0.077 |
| Gastrointestinal bleeding (n, %) | 17 (28.8) | 10 (21.3) | 0.502 |
| Bacterial infection (n, %) | 19 (32.2) | 15 (31.9) | >0.999 |
| Organ failure (n, %) | | | |
| Liver | 6 (10.2) | 26 (55.3) | <0.001 |
| Kidney | — | 25 (53.2) | — |
| Brain | 2 (3.4) | 9 (19.2) | 0.011 |
| Coagulation | 2 (3.4) | 9 (19.2) | 0.011 |
| Cardiac | 3 (5.1) | 8 (17.0) | 0.058 |
| Respiratory | — | 5 (10.6) | — |
| Laboratory values | | | |
| White blood cell ($\times 10^9$/L) | 6.9 (4.8-9.8) | 9.6 (6.3-16.1) | 0.004 |
| C-reactive protein (mg/L) | 11 (5-35) | 29 (9-61) | 0.005 |
| Bilirubin (mg/dL) | 4.2 (1.9-8.3) | 12.9 (4.6-27.3) | <0.001 |
| Prothrombin time (international normalized ratio) | 1.5 (1.4-1.9) | 1.8 (1.5-2.3) | 0.017 |
| Albumin (g/dL) | 3.0 ± 0.7 | 3.1 ± 0.7 | 0.835 |
| Creatinine (mg/dL) | 0.8 (0.6-1.1) | 1.6 (0.9-2.6) | <0.001 |
| Sodium (mmol/L) | 136 (132-139) | 134 (128-140) | 0.318 |
| Platelets ($10^9$/L) | 107 ± 69 | 130 ± 82 | 0.119 |
| MELD | 18 (14-21) | 29 (23-34) | <0.001 |
| MELD Na | 20 (16-25) | 31 (26-36) | <0.001 |
| Child-Pugh score | 9.4 ± 1.9 | 11.0 ± 1.7 | <0.001 |
| CLIF-OFs | 7 (6-8) | 10 (9-11) | <0.001 |
| 28-day mortality (n, %) | 7 (11.9) | 12 (25.5) | 0.079 |
| 3-month mortality (n, %) | 13 (22.0) | 23 (48.9) | 0.004 |

Data are mean ± SD or median (Q1-Q3)

Plasma RIPK3 Level—Human Cohort (FIGS. 1A-1C)

Figure 8:
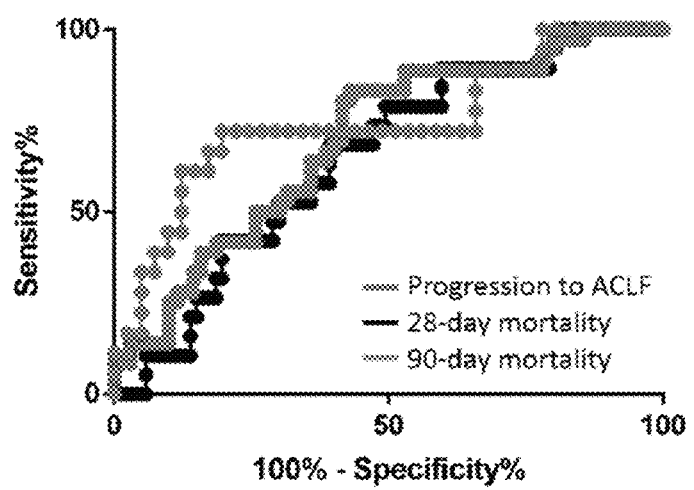
FIG. 8—AUROC values in predicting progression to ACLF, 28-day and 90-day mortality.

The median RIPK3 level for the decompensated group (AD and ACLF combined) was significantly higher than healthy volunteers or stable cirrhosis patients [4559 pg/ml (2302-10604) v 322 pg/ml (136-493) and 445 pg/ml (320-565) respectively, p<0.001, FIGS. 1A and 1C]. Within the decompensated group a statistically significant stepwise increase in RIPK3 level was observed with increasing clinical severity and between ACLF grades [noACLF 2804 pg/ml (1665-5551), ACLF 1 5055 pg/ml (2807-11753), ACLF grade 2+3 11438 pg/ml (7639-23940), p=0.013 and 0.001 respectively, FIGS. 1A and 1C]. In addition, patients who presented with AD but subsequently developed ACLF during hospitalisation had significantly higher levels of RIPK3 than those who remained in AD throughout their admission 5597 pg/ml (1894-9972) v 2513 pg/ml (1563-3683), p=0.003, FIGS. 1B and 1C]. The discrimination power (AUROC) of RIPK3 to predict progression to ACLF was 0.744 (0.593-0.895)(Table 2, FIG. 8). In addition, we observed that RIPK3 plasma levels were statistically higher in non-survivors compared with survivors at 28-day (p=0.037) and 90-day (p=0.001) (Table 2, FIG. 8). The discrimination power (AUROC) of RIPK3 to predict survival was 0.653 (0.530-0.776) and 0.696 (0.593-0.799) at 28- and 90-day, respectively (Table 2, FIG. 8).

TABLE 2

Performance of biomarkers in predicting progression to ACLF, 28 and 90-day mortality

|  | Progression to ACLF AUROC (95% confidence interval) (n = 59) | 28-day mortality AUROC (95% confidence interval) (n = 106) | 90-day mortality AUROC (95% confidence interval) (n = 106) |
|---|---|---|---|
| RIPK3 | 0.744 (0.593-0.895) | 0.653 (0.530-0.776) | 0.696 (0.593-0.799) |
| Nucleosomes | 0.688 (0.554-0.823) | 0.582 (0.478-0.686) | 0.579 (0.477-0.682) |
| cK18 | 0.730 (0.568-0.892) | 0.592 (0.456-0.728) | 0.559 (0.444-0.673) |
| K18 | 0.702 (0.527-0.877) | 0.533 (0.374-0.692) | 0.575 (0.458-0.692) |
| cK18:K18 ratio | 0.527 (0.368-0.686) | 0.541 (0.387-0.694) | 0.550 (0.430-0.669) |
| Child-Pugh score | 0.688 (0.537-0.840) | 0.549 (0.397-0.702) | 0.643 (0.532-0.753) |
| MELD | 0.744 (0.595-0.894) | 0.650 (0.516-0.783) | 0.688 (0.582-0.794) |
| MELD Na | 0.693 (0.541-0.894) | 0.654 (0.521-0.786) | 0.686 (0.573-0.800) |

TABLE 2-continued

Performance of biomarkers in predicting progression to ACLF, 28 and 90-day mortality

|  | Progression to ACLF AUROC (95% confidence interval) (n = 59) | 28-day mortality AUROC (95% confidence interval) (n = 106) | 90-day mortality AUROC (95% confidence interval) (n = 106) |
| --- | --- | --- | --- |
| CLIF-OFs | 0.724 (0.585-0.864) | 0.628 (0.499-0.756) | 0.730 (0.634-0.826) |
| CLIF-C AD score | 0.597 (0.434-0.761) | 0.688 (0.547-0.829) | 0.686 (0.573-0.800) |
| CLIF-C ACLF score | — | 0.634 (0.483-0.785) | 0.720 (0.616-0.824) |

AD, acute decompensation; ACLF, acute on chronic liver failure; AUROC, area under receiver operating characteristic; cK18, caspase-cleaved keratin 18; CLIF-C, chronic liver failure-consortium; CLIF-OFs, chronic liver failure-organ failure score; K18, keratin 18; MELD, model for end-stage liver disease; RIPK3, receptor interacting protein kinase 3.

Figure 9A:
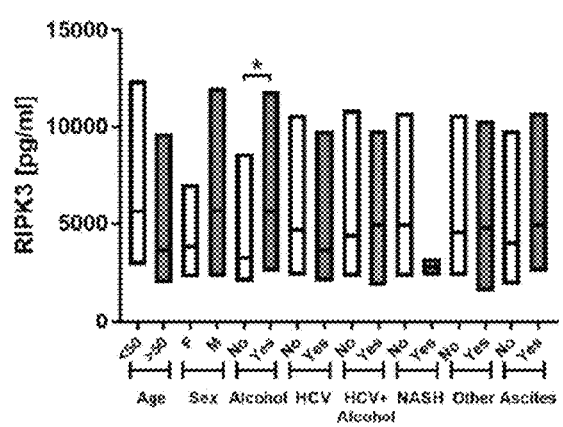
FIGS. 9A-9D—RIPK3 levels in patients with cirrhosis and acute decompensation according to PIRO concept.
Figure 9B:
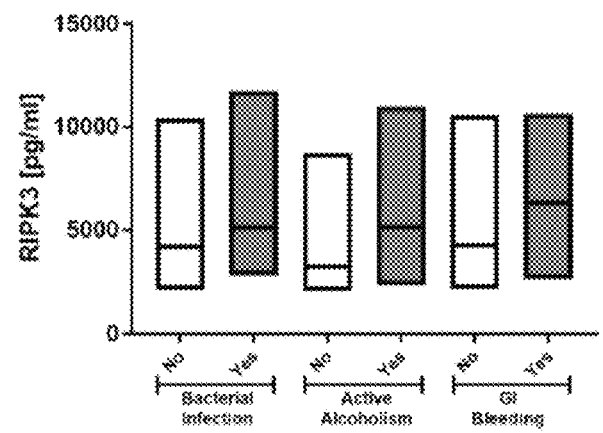
Figure 9C:
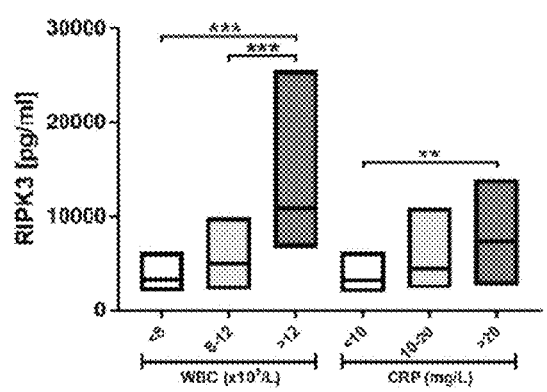
Figure 9D:
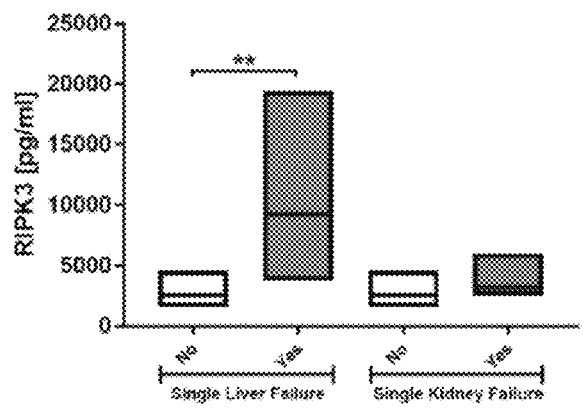

RIPK3 levels were significantly higher in those with alcohol related cirrhosis and also in patients with higher white blood cell count (WBC) and C-reactive protein (FIGS. 9A-9C). RIPK3 levels were higher in those with liver failure compared with no organ failure even when no other organ failure was observed (p=0.001, p=0.019 and p=0.015 respectively) (FIG. 9D) suggesting that the elevated RIPK3 observed in the plasma is likely to be originating from the liver.

Example 2

Immunohistochemistry—Human (FIG. 2)

Increased expression of both RIPK1 and RIPK3 was observed in the liver biopsies of patients with ACLF in addition to alcoholic hepatitis compared to the biopsies of patients with alcoholic hepatitis and no ACLF. Additionally, the distribution of expression also varied between the no ACLF and ACLF groups with the no ACLF group demonstrating speckled intracellular expression whereas the ACLF group displayed specific areas of extensive diffuse expression. The pattern of expression of RIPK1 and 3 were similar. To further investigate whether the increased expression of RIPK1 and RIPK3 lead to transduction of the necroptotic signal downstream we stained the biopsy samples for expression of phosphorylated MLKL, the end point of the necroptotic pathway. The presence of ACLF in addition to alcoholic hepatitis was associated with enhanced expression of phosphorylated MLKL in comparison to alcoholic hepatitis without ACLF.

Example 3

Animal Model of ACLF: Plasma RIPK3 and RIPK1 and 3 Immunohistochemistry—(FIGS. 3A-3B)

Figure 3A:
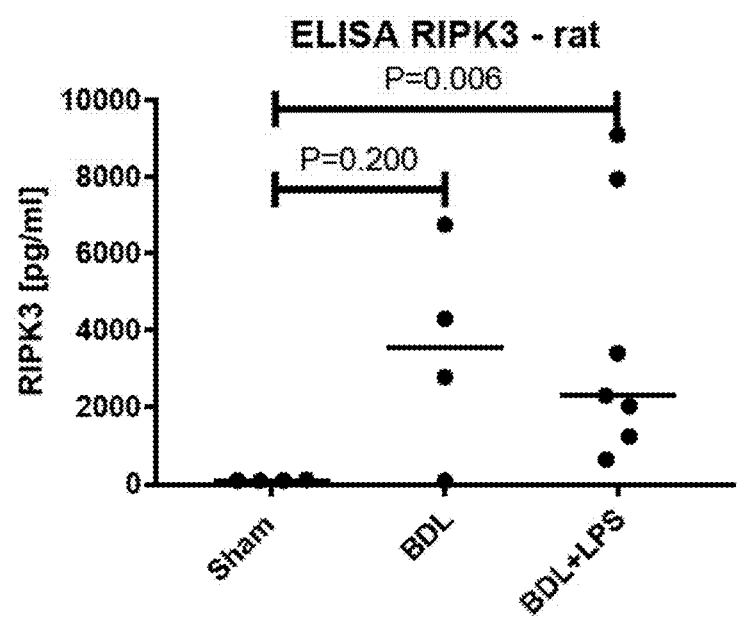
FIGS. 3A-3B—Plasma levels of RIPK3 and RIPK1 and RIPK3 staining in a rodent model of ACLF.
Figure 3B:
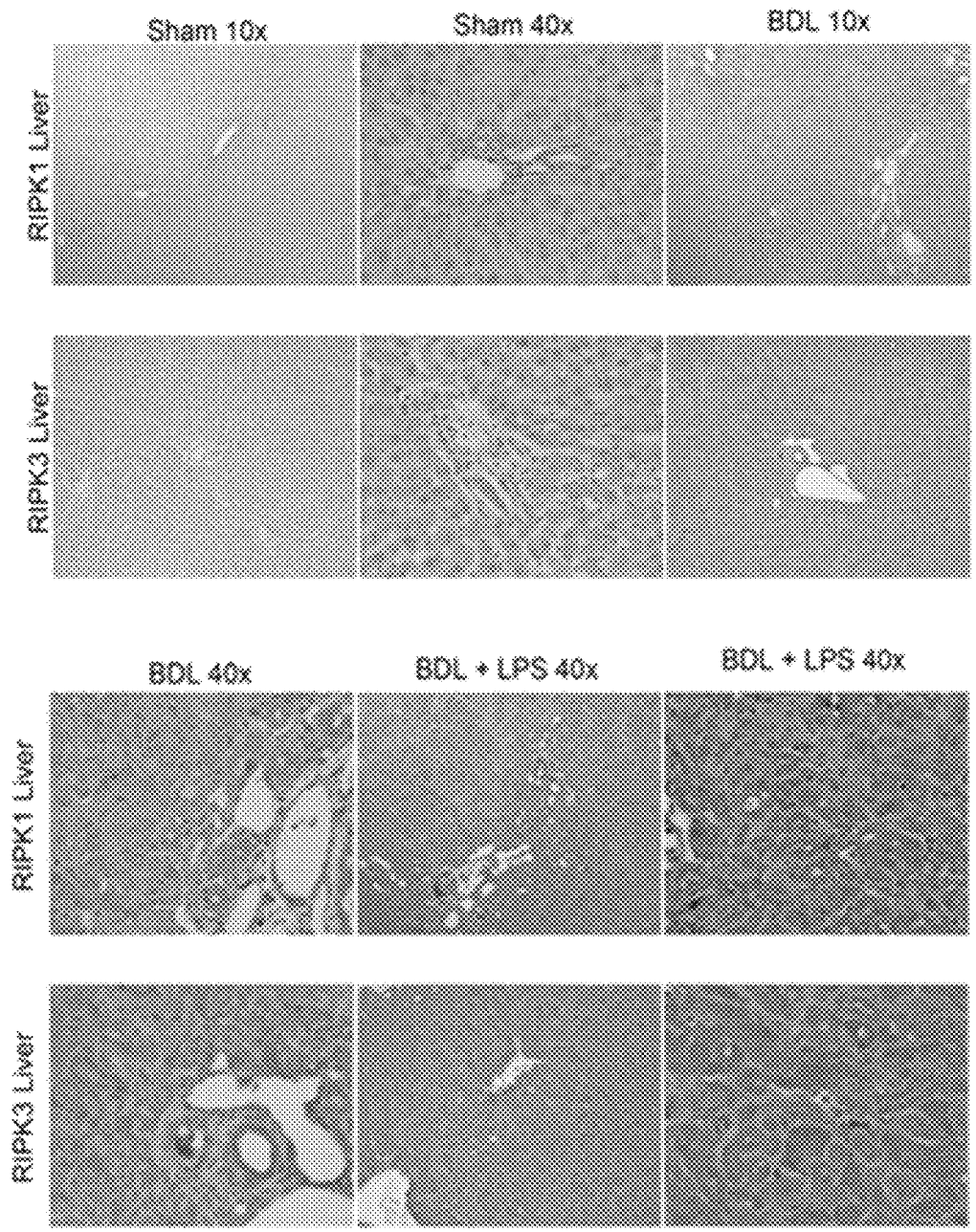
Figure 7A:
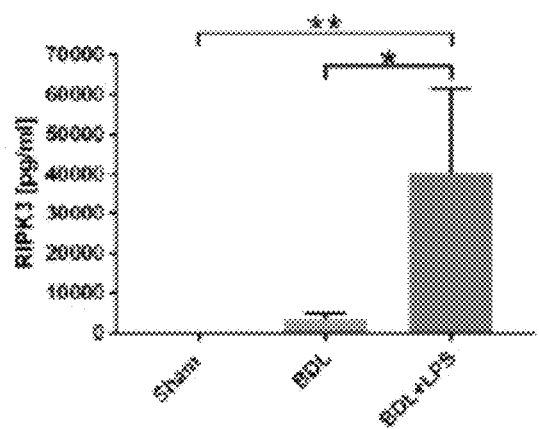
FIGS. 7A-7E—Rat model of ACLF display increased protein expression of RIPK1 and RIPK3 in liver and kidney.
Figure 7B:
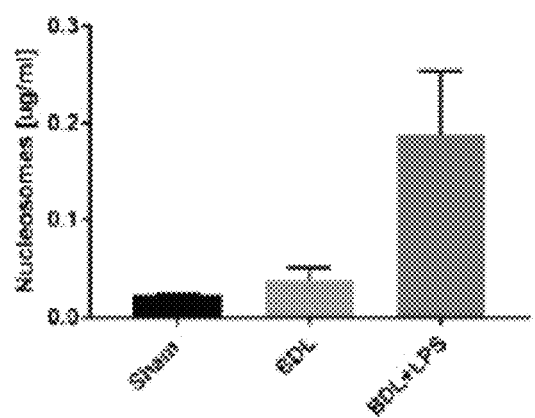

As shown in FIGS. 3A and 7A, elevation of RIPK3 plasma levels was observed in the BDL (cirrhosis) and BDL+LPS (ACLF) animals compared to the sham-operated controls. BDL (cirrhosis) and BDL+LPS (ACLF) animals did not demonstrate significant elevation in circulating nucleosomes or RIPK3 when compared to sham-operated animals (FIG. 7B).

Histologically, very low level of expression of both RIPK1 and 3 was shown in the livers of the sham-operated rats. There was a marked upregulation of both kinases in the BDL group which was drastically exacerbated by the LPS insult in the BDL+LPS treated animals (FIG. 3B).

Figure 7C:
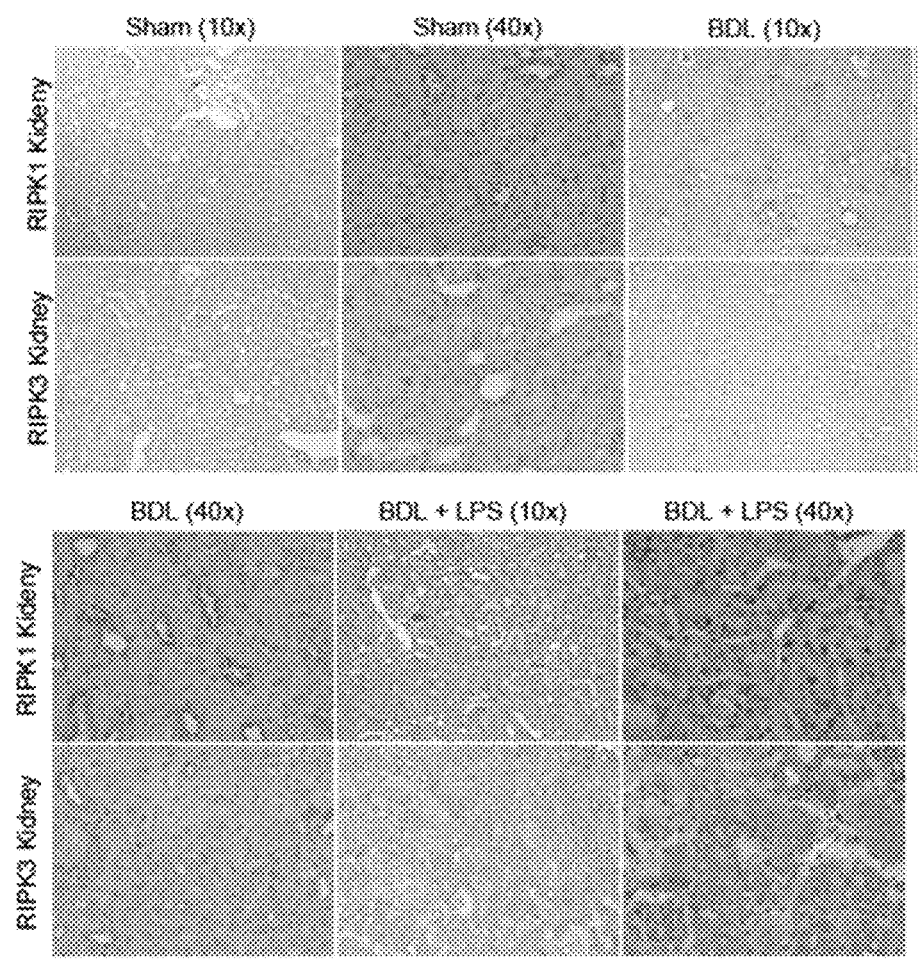
Figure 7D:
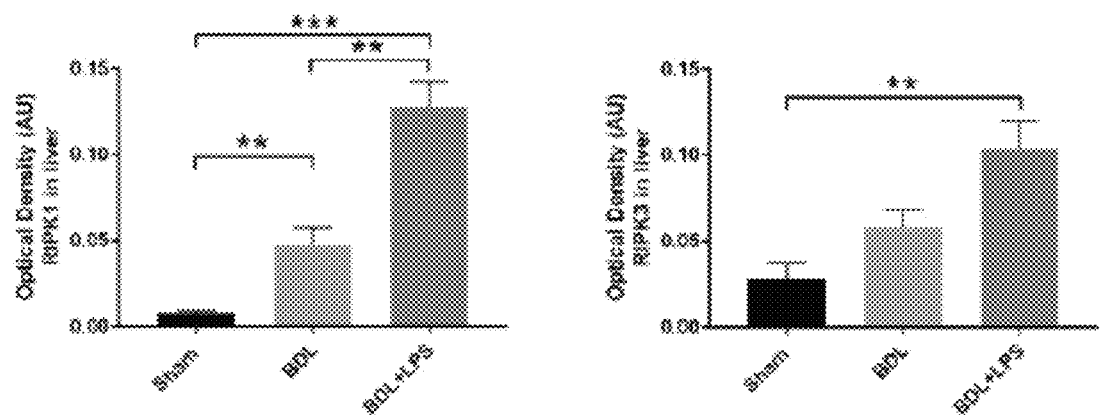
Figure 7E:
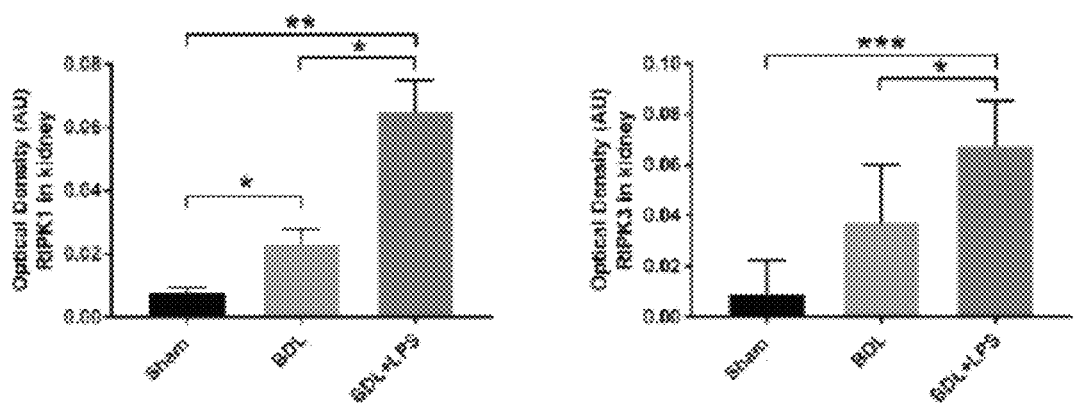

Immunohistochemistry of kidney tissues from BDL animals demonstrated positive staining for RIPK1 and RIPK3 in comparison to sham animals (FIG. 7C). Induction of ACLF in BDL animals by administration of LPS led to significant worsening of liver function tests [alanine aminotransferase (ALT) 79.4±12.8 IU/L; aspartate transaminase (AST) 412.9±39.4 IU/L, p=0.031 compared to BDL] mirrored by increased circulating nucleosomes. In the BDL+LPS animals, a dramatic significant increase in plasma RIPK3 levels was also observed compared to BDL (p=0.042) and this was accompanied by increased protein expression of both RIPK1 and RIPK3 in liver and kidney tissues (FIGS. 3B, 7C, 7D and 7E). These data strongly demonstrate that the onset of ACLF triggered by the administration of LPS to the BDL animals is associated with initiation of necroptosis within 3-hours confirming the findings in the ACLF patients.

Overall, the data from the rodent model recapitulate the features seen in human AD and ACLF patients and, therefore, could be a viable tool for the testing of necroptosis inhibitors in vivo.

Example 4—NEC-1 Treatment Prevents the Occurrence of ACLF in the Rodent ACLF Model It was explored whether treatment with NEC-1, a chemical inhibitor of RIPK1, would prevent ACLF development.

Figure 4A:
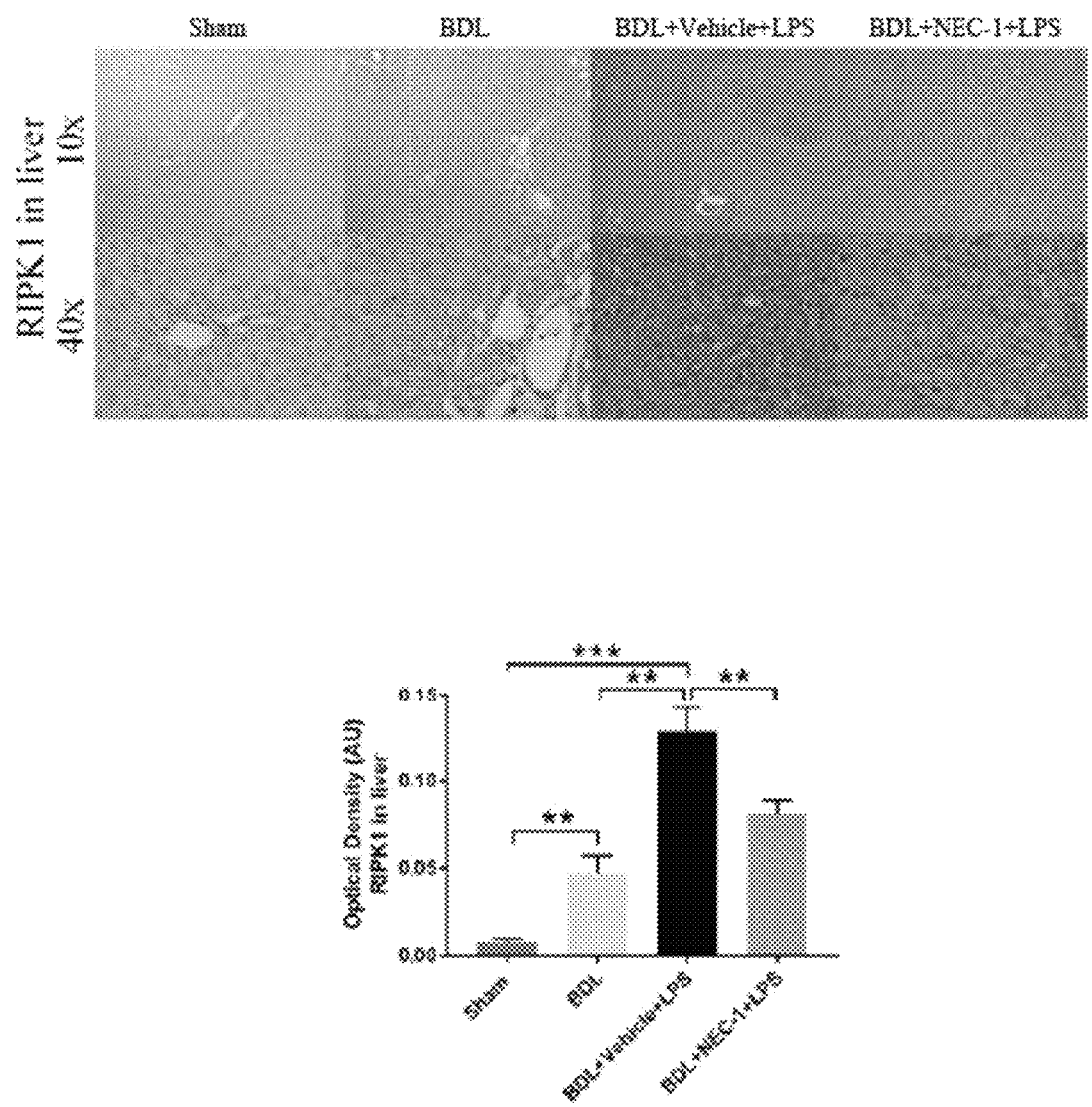
FIGS. 4A-4E—Histological assessment and biomarkers show the protective effect of pharmacological RIPK1 inhibition against ACLF-related liver injury.
Figure 4B:
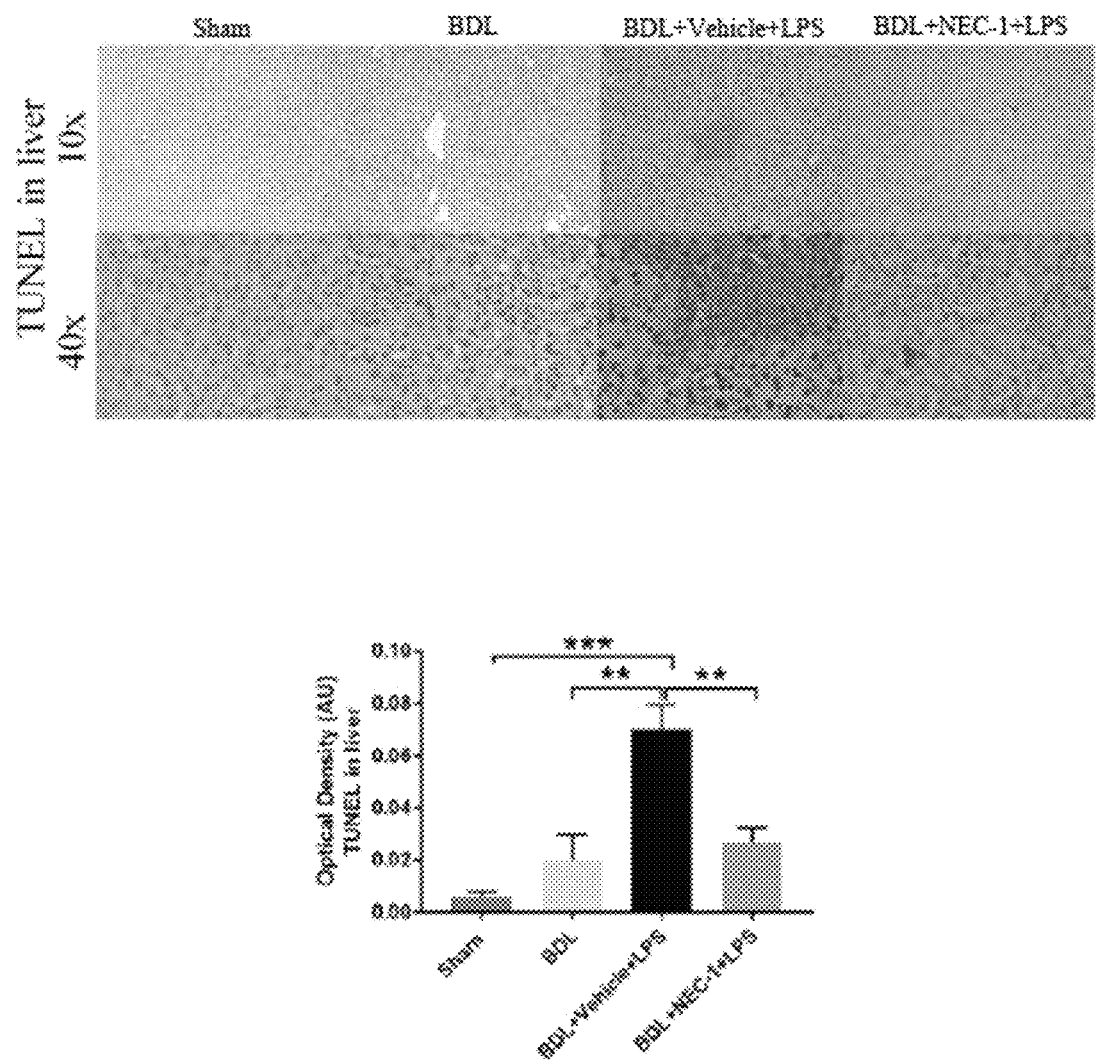
Figure 4C:
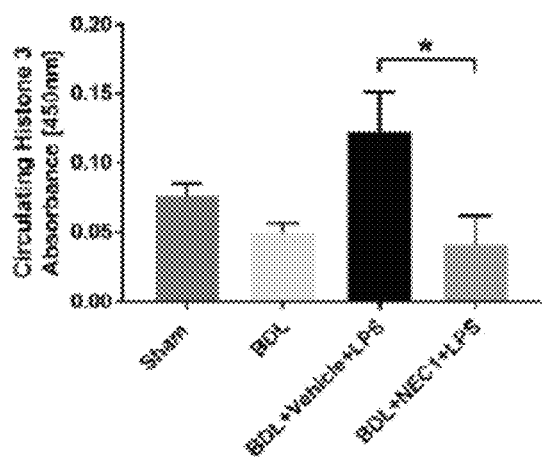

NEC-1 treatment significantly decreased the expression of RIPK1 in NEC-1 treated BDL+LPS group compared to BDL+Vehicle+LPS (p=0.009) (FIG. 4A). Moreover, TUNEL staining showed a significant reduction in total cell death in the livers of the BDL+NEC 1+LPS compared to the BDL+Vehicle+LPS group (p=0.001) (FIG. 4B). This was mirrored by a significant reduction in circulating levels of histone 3, component of nucleosomes and known as DAMPs mediating multiple organ injury34, in the NEC-1 treated group, compared to BDL+Vehicle+LPS animals (p=0.048) (FIG. 4C).

Figure 4D:
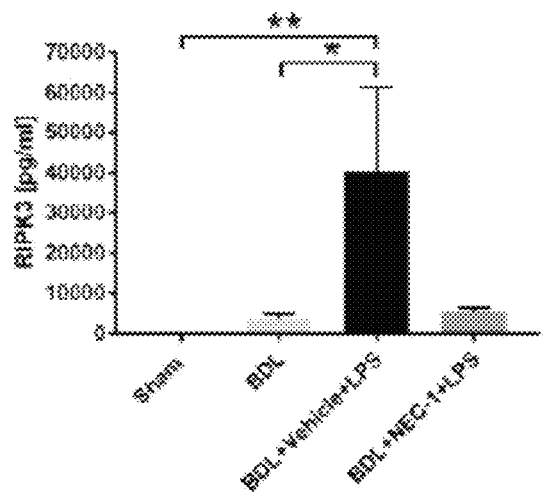
Figure 4E:
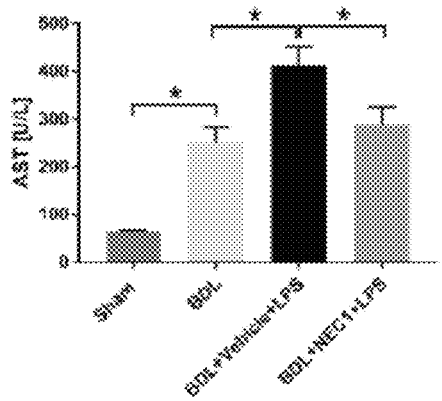
Figure 4E:
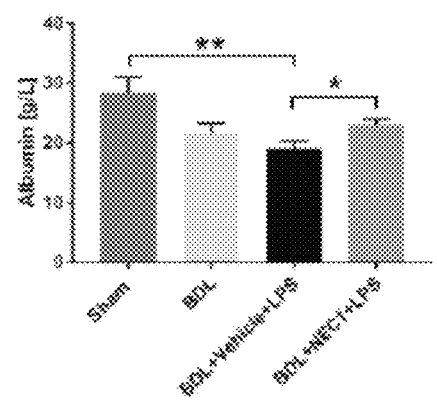

In order to further evaluate whether reduction of necroptosis could account for the observed attenuation of total cell death, circulating levels of RIPK3 were measured. Plasma RIPK3 levels in the BDL+NEC-1+LPS group reduced markedly compared to the BDL+Vehicle+LPS (FIG. 4D). Furthermore, liver preservation by NEC-1 was also demonstrated by significantly lower values of AST (p=0.037) and a significantly higher albumin levels (p=0.017) (FIG. 4E).

Figure 5A:
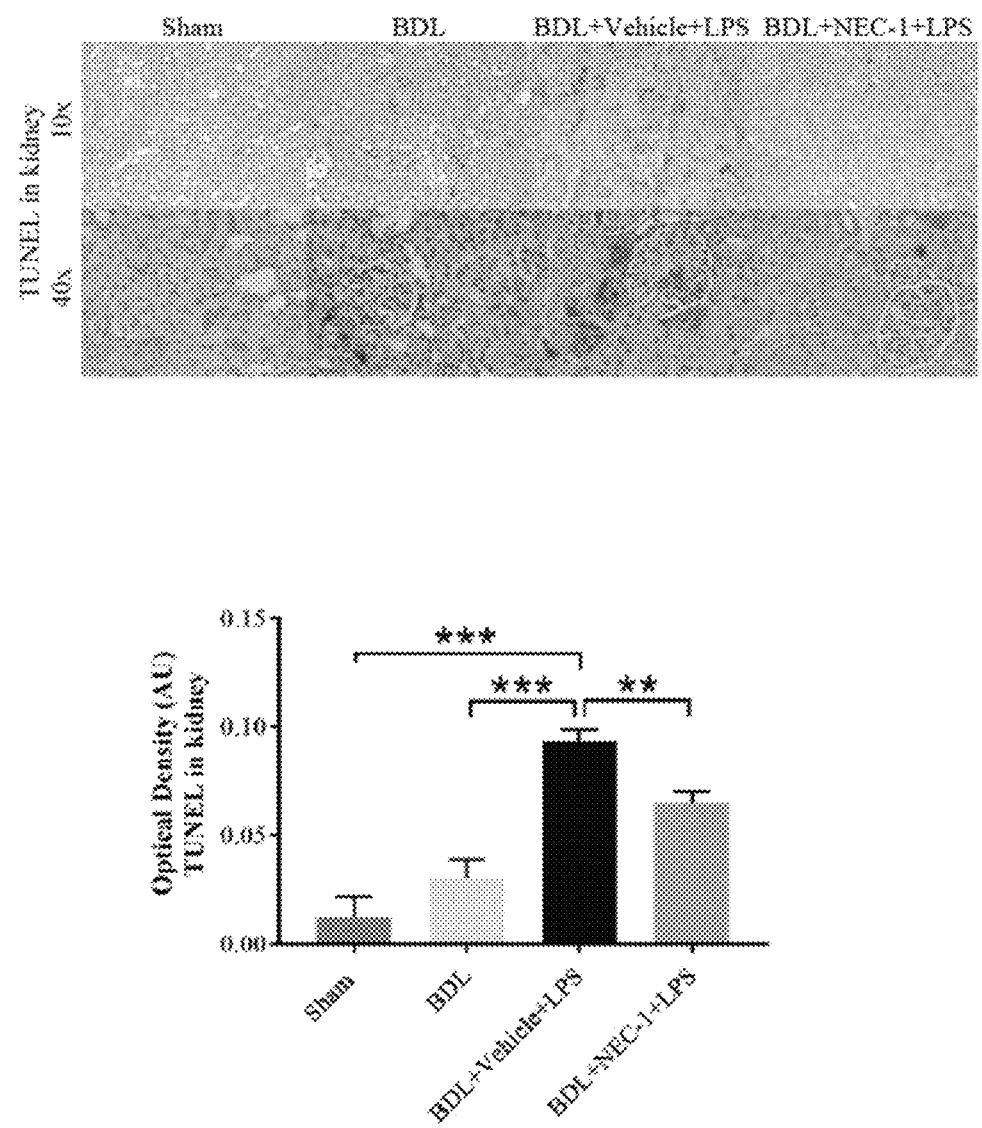
FIGS. 5A-5C—Pharmacological RIPK1 inhibition protects against ACLF-related multiple organ injury.
Figure 5B:
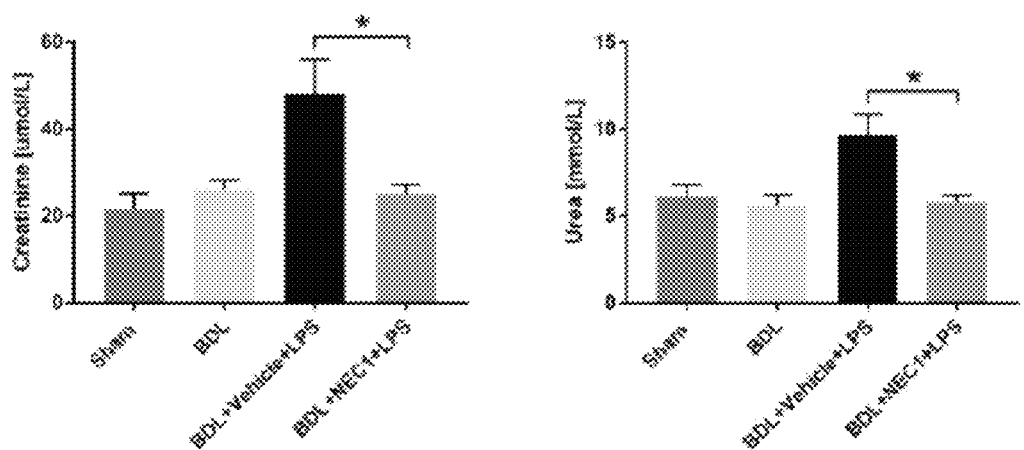
Figure 5C:
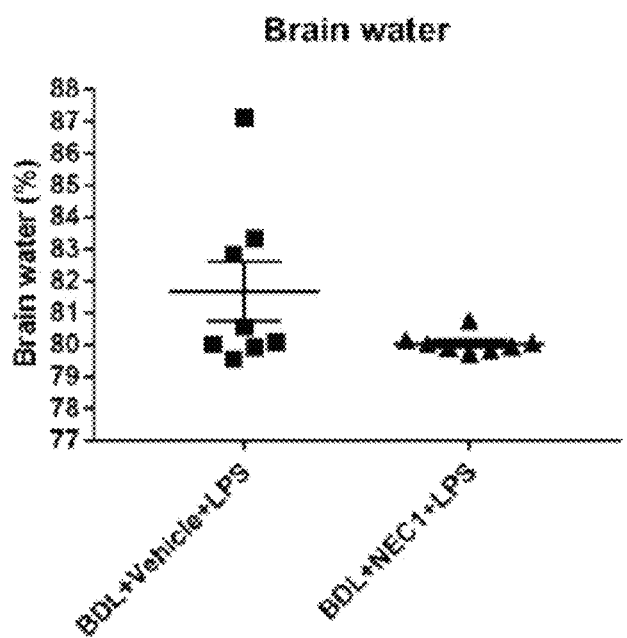

TUNEL staining was then performed in kidney sections to examine kidney/brain dysfunction. A significant reduction in cell death was observed in kidneys of BDL+NEC-1+LPS group compared to BDL+vehicle+LPS (p=0.002) (FIG. 5A). In addition, a significant reduction in creatinine (p=0.020) and urea levels (p=0.012) was observed in BDL+NEC-1+LPS compared to BDL+Vehicle+LPS (FIG. 5B), demonstrating that prevention of liver necroptosis achieved by NEC-1 treatment protects also from kidney dysfunction. In addition, a reduction in brain water content, although not statistically significant, was observed in the BDL+NEC-1+LPS treated group compared to BDL+Vehicle+LPS (p=0.100) (FIG. 5C).

Figure 6:
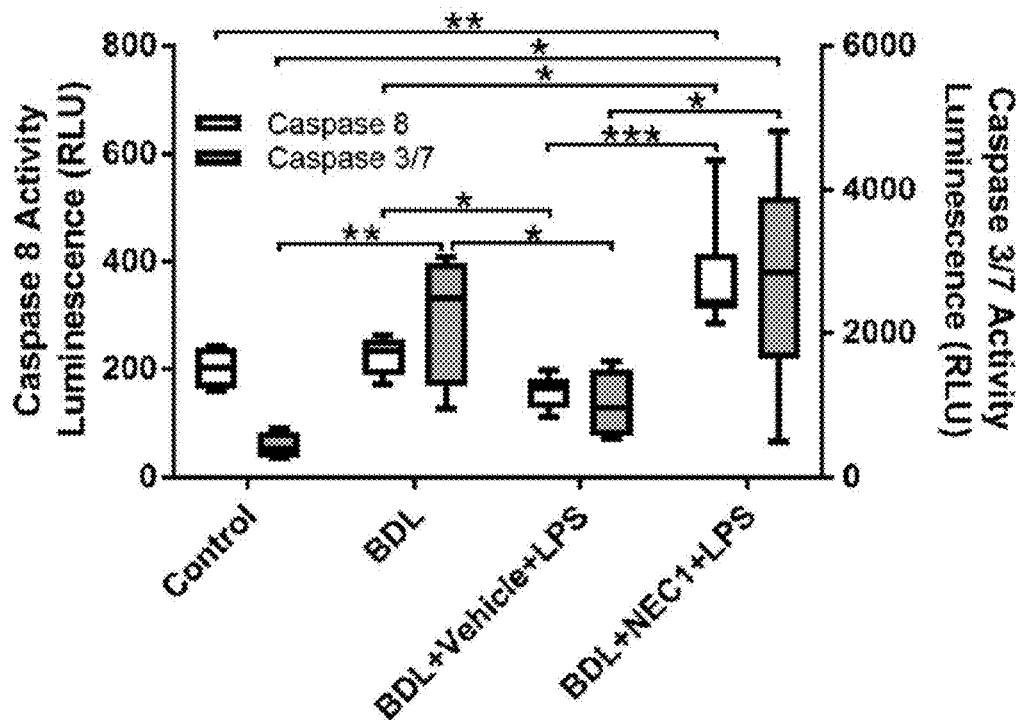
FIG. 6—LPS induces a switch from Caspase-dependent cell death to necroptosis. Caspase 8 and 3/7 activities in liver tissue of sham, BDL, BDL+LPS and BDL+NEC-1+LPS. Data are presented as box and whisker plots. Data were analyzed using Student's t test or Mann-Whitney U test. *$p<0.05$, $p<0.01$, *$p<0.001$.

Example 5—LPS Induces a Switch from Caspase-Dependent Cell Death to Necroptosis The activation pattern of both Caspase 8 and Caspases 3/7 in liver homogenates were investigated. BDL liver showed a significant increase in Caspase 3/7 activation compared to control [median 2492 RLU (IQR 1273-2988) and 396 RLU (IQR 279-630) respectively, p=0.0087] but not in Caspase 8 [median 234.5 (IQR 187.5-255.3) and 202 (IQR 163.8.-239.5) respectively, p=0.425]. In BDL+Vehicle+LPS group a significant reduction of all Caspase activities was observed compared to BDL [Caspase 3/7 [RLU] median 968 RLU (IQR 571-1495), p=0.035; Caspase 8, median 164 RLU (IQR 128-182.5), p=0.021]. NEC-1, inhibiting necroptosis, restored an apoptotic phenotype as demonstrated by sustained activation of Caspases 3/7 and Caspase 8, similar to that observed in the BDL group [Caspase 3/7, median 2857 RLU (IQR 1640-3890); Caspase 8, median 326.5 (IQR 313.5.-414.3), p=0.626 and p=0.020, compared to BDL, respectively] (FIG. 6). Maintaining or agonising caspase 8 activity may therefore be important for suppressing necroptosis.

The invention claimed is:

1. A method of treating or preventing liver failure in an individual in need thereof, said method comprising a step of administering to said individual an antagonist of RIPK1, MLKL or RIPK3, wherein the liver failure is acute-on-chronic liver failure (ACLF).

2. The method of claim 1, wherein the individual is suffering from, or is at risk of one or more of the following, when compared to a subject not suffering from ACLF:
    (a) renal dysfunction, and/or
    (b) renal failure, and/or
    (c) brain dysfunction, and/or
    (d) brain swelling, and/or
    (e) inflammation, injury or dysfunction in the kidney and/or brain, and/or
    (f) liver failure, and/or
    (g) immune failure.

3. The method of claim 1, wherein the individual to be treated has an increased level of serum, liver, urine or plasma RIPK3 compared to the level of RIPK3 in the serum or plasma of an individual not suffering from ACLF.

4. The method of claim 1, wherein administration of said antagonist leads to:
    (a) decreased expression of RIPK1, MLKL or RIPK3 in the liver, immune cells, peripheral blood, kidney and/or brain of the individual; and/or
    (b) decreased levels of RIPK1, MLKL or RIPK3 in the liver, immune cells, peripheral blood, kidney and/or brain of the individual; and/or
    (c) decreased activity of RIPK1, MLKL or RIPK3 in the liver, immune cells, peripheral blood, kidney and/or brain of the individual.

5. The method of claim 1 wherein the liver failure is caused by aberrant necroptosis.

* * * * *